United States Patent [19]
Wissenbach et al.

[11] Patent Number: 5,633,809
[45] Date of Patent: May 27, 1997

[54] MULTI-FUNCTION FLOW MONITORING APPARATUS WITH AREA VELOCITY SENSOR CAPABILITY

[75] Inventors: Richard Wissenbach, Brockport; Anthony Tavano, Niagara Falls, both of N.Y.

[73] Assignee: American Sigma, Inc., Medina, N.Y.

[21] Appl. No.: 635,054

[22] Filed: Apr. 19, 1996

Related U.S. Application Data

[63] Continuation of Ser. No. 547,718, Oct. 26, 1995, abandoned, which is a continuation-in-part of Ser. No. 219,097, Mar. 29, 1994, Pat. No. 5,506,791, which is a continuation-in-part of Ser. No. 954,288, Sep. 30, 1992, Pat. No. 5,299,141, which is a continuation-in-part of Ser. No. 612,832, Nov. 13, 1990, Pat. No. 5,172,332, which is a continuation-in-part of Ser. No. 455,981, Dec. 22, 1989, Pat. No. 5,091,863.

[51] Int. Cl.[6] .................................................. G06F 17/00
[52] U.S. Cl. ............................................................ 364/510
[58] Field of Search .................................... 364/509, 510; 73/863.01, 863, 863.02, 863.03, 864.34, 515; 141/1, 89, 91, 94, 130; 422/82.11, 98; 385/12; 367/13

[56] References Cited

U.S. PATENT DOCUMENTS

| Re. 33,064 | 9/1989 | Carter et al. ...................... 422/82.11 |
| 3,295,127 | 12/1966 | Kross . |
| 3,507,156 | 4/1970 | Merrill, Jr. ........................... 73/863.02 |
| 3,727,464 | 4/1973 | Rutkowski et al. ................. 73/863.01 |
| 3,838,719 | 10/1974 | Lederer .................................... 141/284 |
| 3,927,701 | 12/1975 | Lederer ...................................... 141/98 |
| 3,929,017 | 12/1975 | Kowalski ............................... 364/510 X |
| 3,940,731 | 2/1976 | Cooper et al. . |
| 3,996,786 | 12/1976 | Mead et al. ................................ 73/53 X |
| 4,022,059 | 5/1977 | Schontzler et al. ................. 141/130 X |
| 4,050,895 | 9/1977 | Hardy et al. ................................ 422/98 |
| 4,145,925 | 3/1979 | Stasz et al. . |

(List continued on next page.)

Primary Examiner—Ellis B. Ramirez
Attorney, Agent, or Firm—Weiner, Carrier & Burt, P.C.; William F. Esser; Irving M. Weiner

[57] ABSTRACT

A multi-function fluid flow monitoring apparatus capable of measuring fluid flow-related variables of fluid in a channel on the basis of signals from any one or more of a plurality of different types of flow sensors. Such different types of flow sensors may include, for example, a bubbler-type pressure sensor, a submerged pressure transducer, an ultrasonic transducer, and/or a velocity sensor forming part of an area-velocity sensor system, each of which sensors may be selectively connected to the apparatus as needed to accommodate various monitoring conditions. The apparatus is further capable of monitoring various conditions of fluid in the channel, such as pH level, ORP, temperature, solution conductivity, dissolved oxygen, and the like. In addition, the apparatus may be selectively linked with one of a variety of operational devices, such as an automatic sampling apparatus, a rain gauge, or a pump, so as to selectively initiate desired actions by such external device(s) or to otherwise operably cooperate with such external device(s). The integral operating unit includes a computer control system including a microprocessor, program memory, and data memory. External connectors are provided for selective connection to one or more different flow sensors, fluid condition sensors, and/or external devices. The apparatus further includes a display screen, controlled by the computer control system, which selectively displays data in either text or graphics formats. Data including flow-related data, fluid condition data, as well as data from external devices, may be transferred from the data memory of the apparatus to an external computer, printer, or the like by use of a hand-held data transfer unit or a modem integrally provided in the apparatus. The apparatus includes a liquid velocity measurement unit based upon Doppler technology, comprising a spectrum analyzer for calculating average fluid velocity, a mechanism for calculating maximum fluid velocity, and a means for verifying the calculated average fluid velocity based upon the calculated maximum fluid velocity value.

27 Claims, 24 Drawing Sheets

U.S. PATENT DOCUMENTS

| | | | |
|---|---|---|---|
| 4,221,127 | 9/1980 | McClure | 73/861 |
| 4,257,278 | 3/1981 | Papadofrangakis et al. | |
| 4,397,191 | 8/1983 | Forden . | |
| 4,660,422 | 4/1987 | Eads et al. | 73/863.02 |
| 4,660,607 | 4/1987 | Griffith et al. | 141/1 |
| 4,697,462 | 10/1987 | Daube, Jr. et al. | 73/862.02 X |
| 4,710,353 | 12/1987 | Tanaka et al. | 422/82.11 |
| 4,766,550 | 8/1988 | Byers et al. | 73/863.01 X |
| 4,799,169 | 1/1989 | Mims | 73/510 |
| 4,846,548 | 7/1989 | Klainer | 385/12 |
| 5,020,374 | 6/1991 | Petroff et al. . | |
| 5,091,863 | 2/1992 | Hungerford et al. | 364/510 |
| 5,095,514 | 3/1992 | Curtis | 385/12 |
| 5,096,671 | 3/1992 | Kang et al. | 385/12 |
| 5,156,927 | 10/1992 | Issachar | 422/82.11 |
| 5,172,332 | 12/1992 | Hungerford et al. | 73/863.01 |
| 5,176,882 | 1/1993 | Gray et al. | 385/12 |

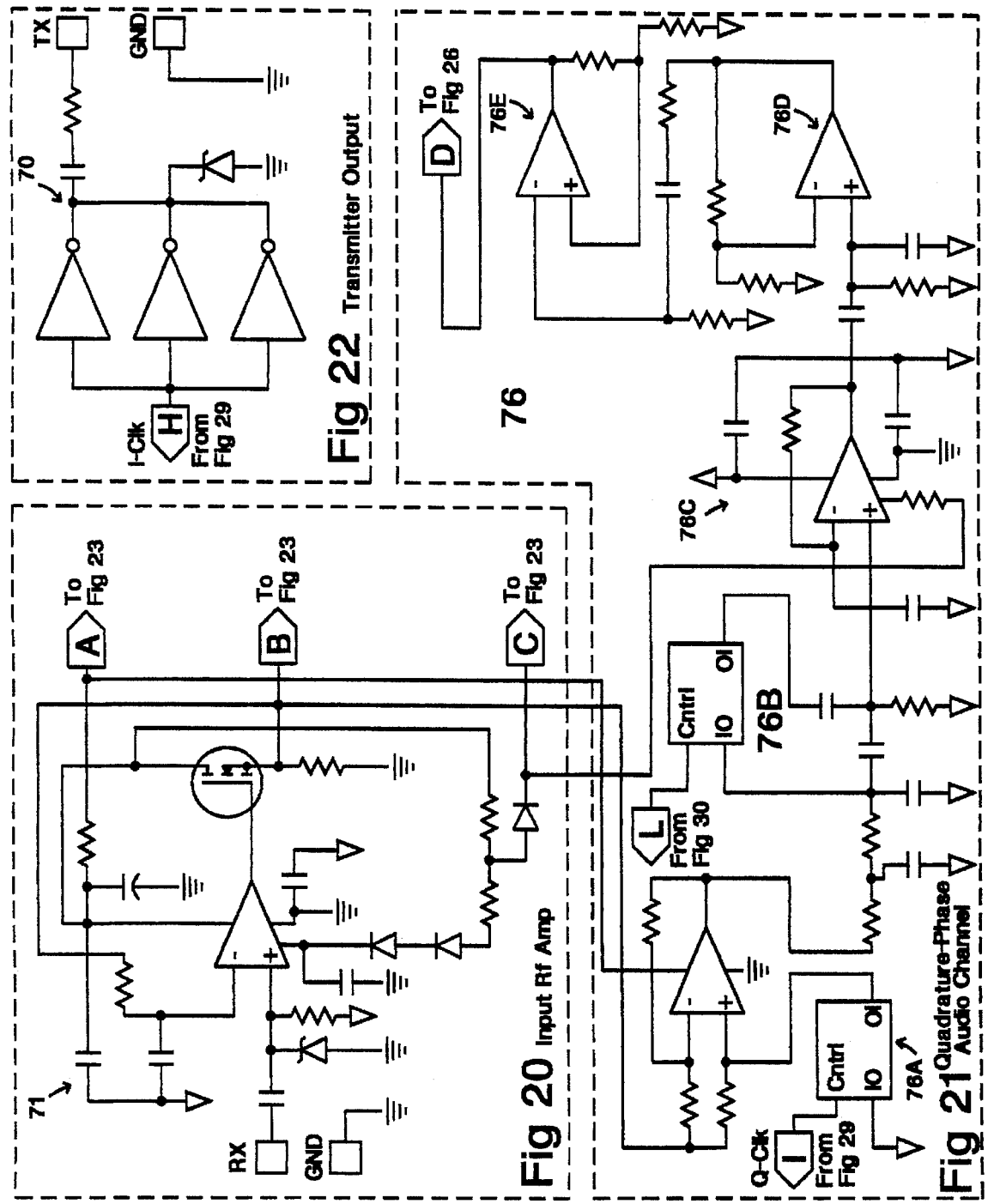

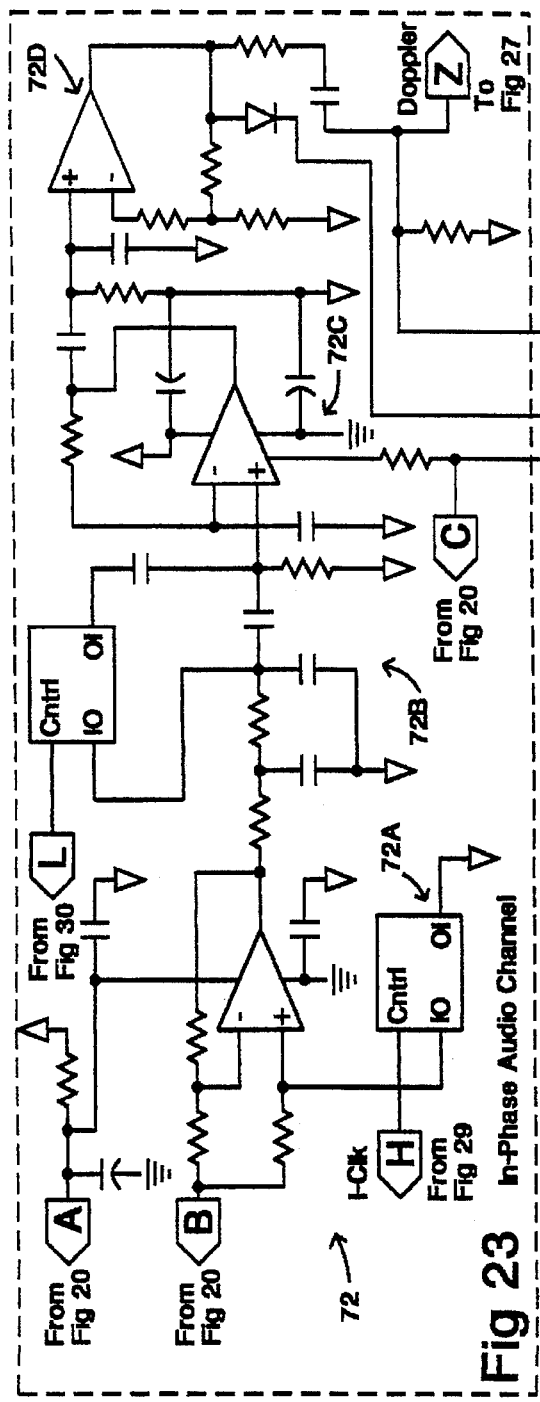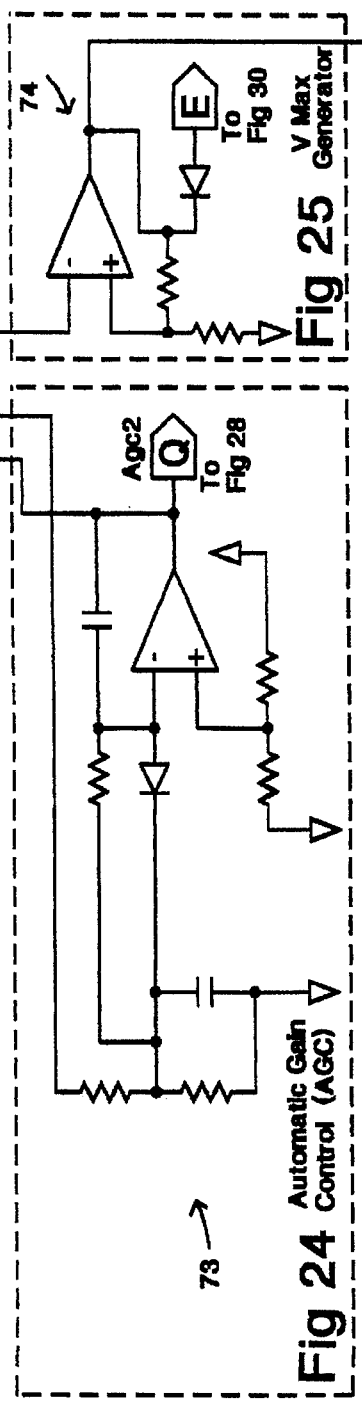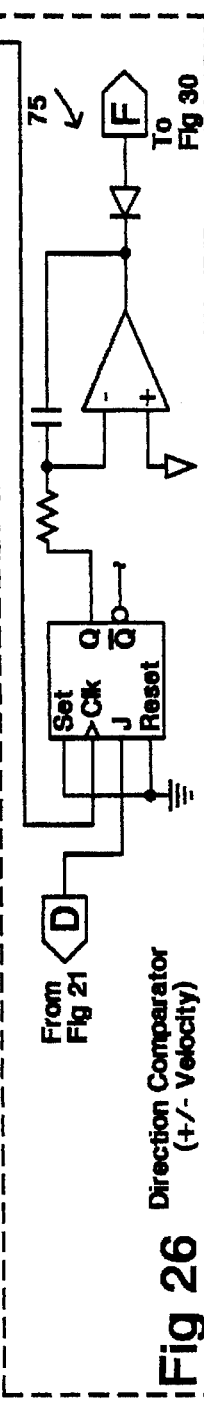
Fig 23 In-Phase Audio Channel
Fig 24 Automatic Gain Control (AGC)
Fig 25 V Max Generator
Fig 26 Direction Comparator (+/- Velocity)

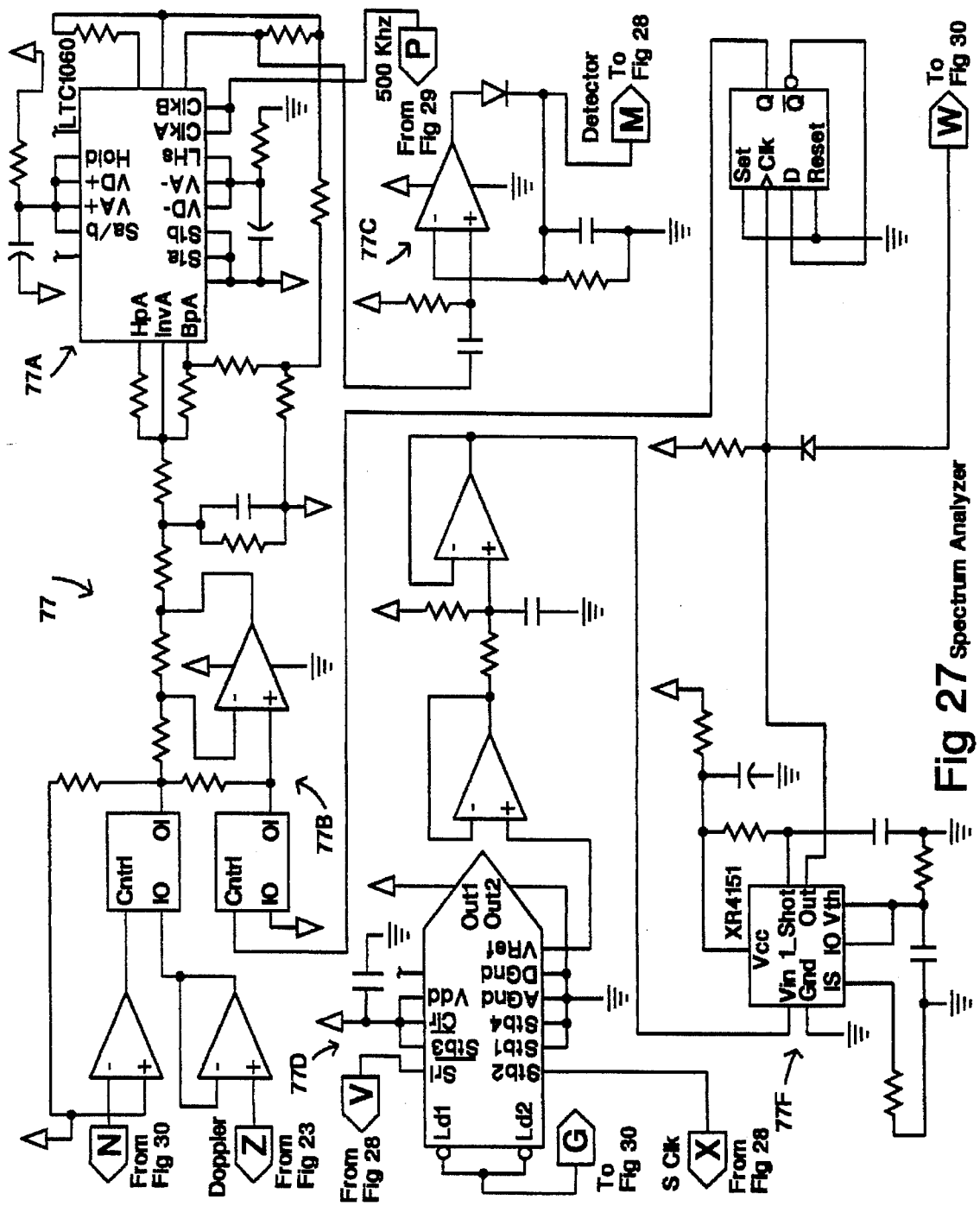
Fig 27 Spectrum Analyzer

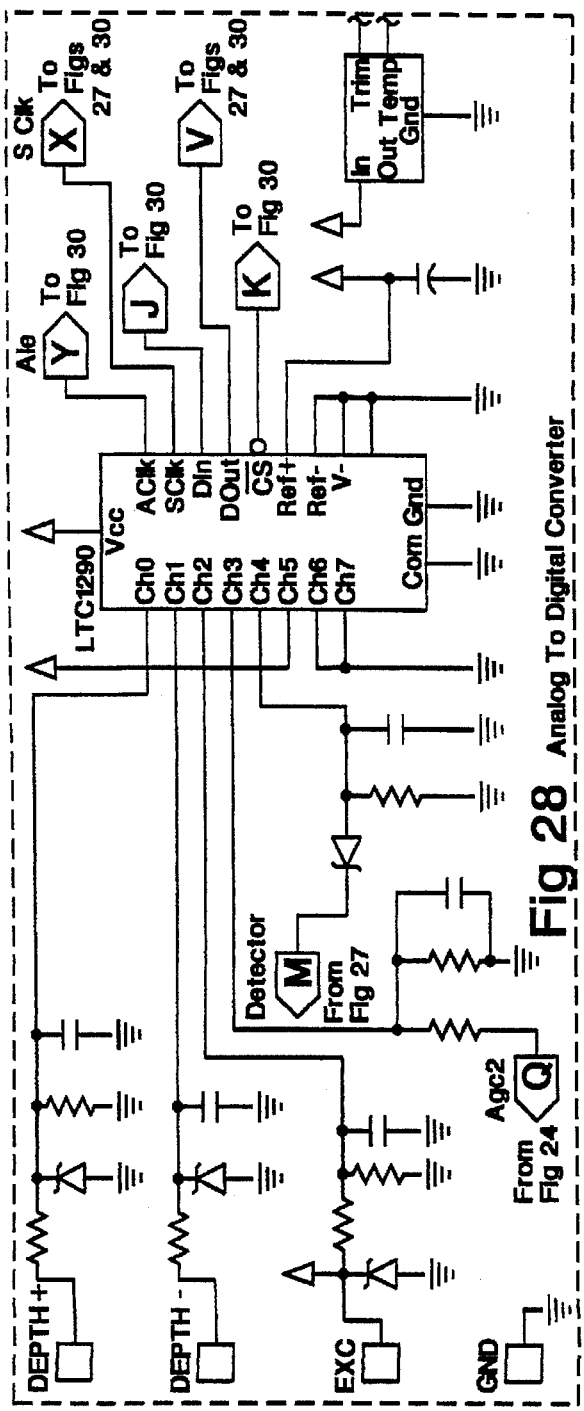
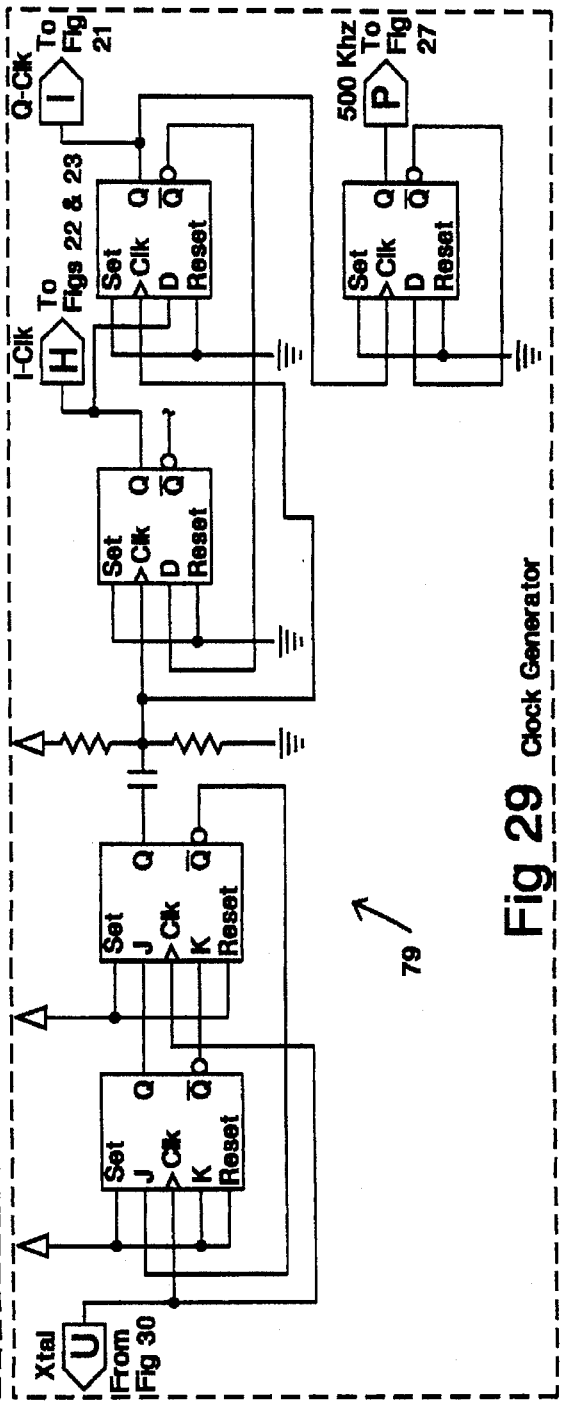
Fig 28 Analog To Digital Converter
Fig 29 Clock Generator

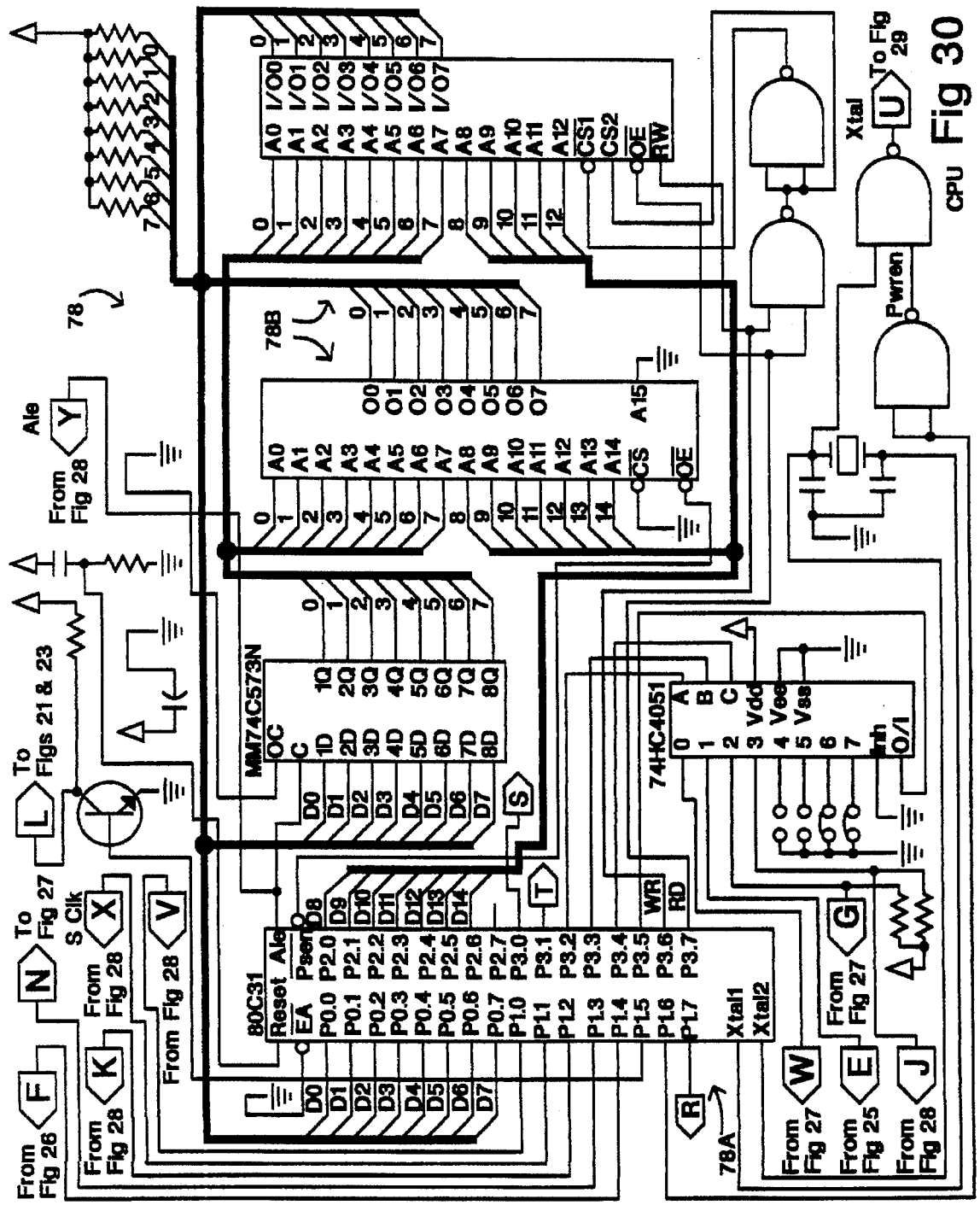

MULTI-FUNCTION FLOW MONITORING APPARATUS WITH AREA VELOCITY SENSOR CAPABILITY

This is a file wrapper continuation of application Ser. No. 547,718, which was filed Oct. 26, 1995 now abandoned; which in turn is a continuation-in-part of application Ser. No. 219,097, which was filed Mar. 29, 1994, now U.S. Pat. No. 5,506,791; which in turn is a continuation-in-part of application Ser. No. 954,288 filed Sep. 30, 1992 which issued as U.S. Pat. No. 5,299,141; which is in turn a continuation-in-part of application Ser. No. 612,832 filed Nov. 13, 1990 which issued as U.S. Pat. No. 5,172,332; which is in turn a continuation-in-part of application Ser. No. 455,981 filed Dec. 22, 1989 which issued as U.S. Pat. No. 5,091,863. The disclosure of each of such applications and patents is incorporated herein by reference thereto.

BACKGROUND OF THE INVENTION

1. Field of the Invention

The present invention relates generally to a multi-function fluid flow monitoring apparatus having the unique capability of measuring fluid flow-related variables on the basis of outputs from any one or more of a plurality of different types of flow sensors. In accordance with the multi-functional features of the invention, the apparatus can also perform fluid monitoring operations and can be linked to a variety of devices, such as an automatic sampler, a rain gauge, and the like so as to operably cooperate with same. The apparatus also provides for the displaying, storing, and transferring of data relating to fluid flow measuring and monitoring operations.

More particularly, the invention relates to a compact unitary apparatus having a computer control system which calculates fluid flow-related variables on the basis of outputs from any desired one or more of a plurality of different types of flow sensors which may be selectively and interchangeably connected to the apparatus. By virtue of this multiple flow sensor capability, the user is provided with substantial flexibility in selecting a flow sensor system suitable for a given application, and then selectively switching to any desired one of a plurality of other types of sensor systems as the need arises. The user is also afforded the flexibility of investing in a basic apparatus including, for example, a single type of flow sensor, and then later expanding the range of use of the apparatus by investing in additional types of flow sensors which are all fully compatible with, and supported by, the basic apparatus.

The apparatus of the invention also comprises a text and graphics display which permits a user to selectively view stored data in either text or graphic formats. Stored data can also be transferred to a computer for manipulating data or producing hard copy reports.

The invention also provides a novel bubbler sensor type fluid flow monitoring system comprising a novel bubbler control module which overcomes power consumption and inaccuracy problems associated with conventional bubbler sensor systems. The bubbler sensor flow monitoring system according to the invention is incorporated in the multi-function flow monitoring apparatus with multiple flow sensor capability. In an alternative embodiment, the bubbler sensor flow monitoring system of the invention may be provided independently in a flow measuring device having only a single sensor capability.

The terminology "flow sensors" as used herein refers to various available types of sensors for detecting a variable related to fluid flow and producing an electrical output signal corresponding thereto. Such sensors include, but are not limited to, bubbler-type pressure sensors, submerged pressure transducers, ultrasonic sensors, area-velocity sensor systems, and the like.

The terminology "fluid flow-related variables" as used herein embraces a multitude of fluid flow parameters, including fluid level or depth, flow rate, velocity, total flow, i.e., the actual quantity of fluid discharged over a given time period, and the like.

In addition to the versatility afforded by the interchangeability of different flow sensors, the apparatus of the invention may also provide fluid monitoring capabilities similar to those described in the aforesaid U.S. Pat. No. 5,172,332, by attaching an appropriate fluid condition sensor to the fluid flow monitoring apparatus of the invention. These monitoring capabilities enable the apparatus to calculate the value of a given fluid condition on the basis of inputs from a fluid condition sensor. By way of example, such fluid conditions may include pH level, oxidation reduction potential ("ORP"), temperature, solution conductivity or resistivity, dissolved oxygen, etc.

The apparatus according to the invention may further include means for automatically sampling fluids similar to that disclosed in the aforesaid U.S. Pat. Nos. 5,091,863 or 5,172,332. The user may then instruct the apparatus to initiate sampling operations on the basis of fluid flow related variables, or on the basis of high, low, or a range of critical levels of fluid condition(s) as calculated by the apparatus. The apparatus of the invention also automatically calculates and stores fluid flow-related variables and levels of fluid conditions to permit tracking of the history of the fluid conditions in a process stream. In a preferred embodiment, the present invention is selectively capable of isolating collected samples pertaining to a fluid flow variable or a critical fluid condition as calculated and/or detected by the apparatus, so as that collected samples representing a problem or out-of-limit condition can be quickly identified, thereby reducing laboratory analysis and analysis costs.

The apparatus according to the invention may also initiate desired actions based on fluid flow-related variables or fluid condition(s) values calculated by the apparatus. For example, the apparatus may activate a pump so as to initiate a pumping operation when water level rises above a predetermined level. It is further contemplated that the apparatus according to the invention may be selectively connected to other external devices, such as a rain gauge, so as to log data therefrom.

2. Description of the Relevant Art

Under current governmental statutes and regulations, municipal agencies and private organizations are required to carefully monitor fluid waste. Monitoring is also conducted for pollution research purposes and the like. By way of example, monitoring is typically conducted in the following applications: monitoring for compliance with NPDES permits; POTW compliance monitoring; storm water run-off monitoring; combined sewer overflow ("CSO") monitoring; pretreatment compliance; WWTP process control; and infiltration and inflow studies.

In these and similar monitoring applications, one of the principal devices used on-site is a flow meter. In addition to monitoring various fluid flow-related variables, the flow meter may also be used for pacing sampling operations in proportion to flow rate, i.e., in conjunction with a sampling apparatus which repeatedly collects samples for subsequent laboratory analysis. A separate analytical meter is also often used for on-site monitoring of critical fluid conditions, such as pH level or ORP, to alert the user in a relatively immediate fashion to an upset in the process stream. Because flow meters, analytical devices and samplers are regularly transported to and mounted at remote field sites, it is desirable for each piece of equipment to be as compact, versatile, and easy to use as possible.

The present inventors, in the apparatus disclosed in their aforesaid U.S. Pat. No. 5,091,863, have overcome many of the problems associated with using separate samplers and flow meters by providing an integrated, compact automatic sampling and flow measuring apparatus capable of pacing sampling in proportion to flow rate, and of storing sample collection and flow data for retrieval in hard copy form.

In the apparatus disclosed in their aforesaid U.S. Pat. No. 5,172,332, the present inventors have also overcome the problems associated with separate automatic sampler and analytical meter devices. The apparatus combines a sampler and analytical meter in a single unitary structure, with the sampler and analytical meter sharing the same computer control means, digital display, keyboard, circuitry, etc. The computer control means of the apparatus automatically calculates the values of fluid condition(s) such as pH level, and controls sampling operations on the basis of time and/or fluid condition(s). The apparatus also stores sample collection and fluid condition(s) data for later retrieval by the user.

The multi-function apparatus of the present invention is particularly directed to solving problems associated with transporting and using flow meters at remote monitoring sites. Technicians in the field encounter a variety of different conditions at different sampling sites, sewer manholes, and other monitoring environments, so that different types of flow sensors are required to accommodate varying open channel flow applications. Heretofore, it has been necessary to use different flow meter devices, each adapted to operate with only a single sensor type, to accommodate varying field conditions. For example, where an ultrasonic flow sensor would be best suited for a particular application, the user would have to acquire and transport a separate flow meter having an ultrasonic flow sensor. Subsequently, if the user were to encounter field conditions for which a bubbler-type flow sensor would be most suitable, the user would have to acquire and transport a different flow meter having a bubbler-type sensor.

The expense and inconvenience entailed by the use of different flow meters is eliminated by the present invention, in which the same compact apparatus accommodates a variety of interchangeable flow sensors. The multi-function fluid monitoring apparatus of the present invention has a compact, unitary structure incorporating a microprocessor which is programmed to automatically calculate and store data, as well as to perform other functions. A principal advantage afforded by the present invention is that the same compact fluid monitoring apparatus accommodates a plurality of different types of interchangeable flow sensors. Other advantages afforded by the invention include the selective graphic or tabular display of stored data in a convenient form for the user, the capability of monitoring various fluid conditions in addition to fluid flow-related variables, and features such as automatic fluid sampling. These and other features of the apparatus according to the invention render it multi-functional and highly versatile in use, while providing a structure which is very compact, conveniently transportable, and minimizes expense.

SUMMARY OF THE INVENTION

The invention provides an apparatus for monitoring at least one flow-related variable of fluid flow in a channel, comprising an integral operating unit provided in a unitary case, the integral operating unit including computer means for controlling the apparatus and input means for receiving detected signals related to fluid flow in the channel. The input means is selectively connectable to any selected one or more of a plurality of different types of flow-sensing means for producing signals related to the fluid flow in the channel. The integral operating unit further includes means for processing the signals from each of the plurality of different types of flow-sensing means, for input to the computer control means. The apparatus is also provided with power means for supplying power to each element of the apparatus. The computer control means comprises a microprocessor, program memory, and data memory. The data memory stores user-selected input parameters including at least one fluid flow-related parameter, and may further store fluid flow-related data. The microprocessor receives the signals related to fluid flow from the processing means and calculates values of at least one flow-related variable based on the signals, the user-input fluid flow-related parameter, and a selected one of a plurality of equations for computing values of the flow-related variable. Preferably, the plurality of equations are stored in the program memory of the computer control means.

In a preferred embodiment, a plurality of flow sensor control modules incorporate the signal processing means and other interface means, with each control module being associated with a particular type of flow sensor. The plurality of flow sensors may preferably include at least a bubbler sensor, a submerged sensor, an ultrasonic sensor, and a velocity sensor.

The bubbler sensor control module of the invention comprises, in addition to the signal processing means, an air pump operatively connected with an air reservoir so as to pressurize same, air flow restriction means connected to the reservoir, first pressure sensing means connected between the air flow restriction means and the reservoir, and second pressure sensing means connected downstream of the reservoir. The external connector associated with the bubbler sensor is connected to the air pump downstream of the second pressure sensing means. The microprocessor receives signals from the first and second pressure sensing means, and calculates the difference in pressure between the first and second pressure sensing means. The microprocessor is connected to the air pump so as to operate the pump to maintain a predetermined pressure difference between the first and second pressure sensing means. By virtue of this arrangement, the pressure across the air flow restrictor is kept constant, so that a nearly constant air flow or bubble rate is maintained in the fluid channel. The arrangement results in decreased power consumption and increased accuracy relative to known arrangements. In an alternative embodiment, the novel bubbler flow sensing system of the invention may be incorporated in a single-sensor type flow meter.

It is an object of the invention to provide a fluid flow monitoring apparatus which is completely contained in a compact, unitary case and which has the capability of measuring fluid flow-related variables on the basis of outputs from any one or more of a plurality of different types of flow sensors. The invention thus eliminates the expense and inconvenience associated with having to employ a number of different flow meters which each support only a single type of flow sensor.

In accordance with another important object of the invention, the flow monitoring apparatus is integrally provided with one or more fluid condition monitoring assemblies or modules which are connected with the microprocessor of the apparatus so as to input signals thereto from one or more fluid condition sensors, such as a pH sensor, ORP sensor, dissolved oxygen sensor, solution conductivity sensor, and/or other fluid condition sensors. The apparatus is thus provided with multi-functional capabilities to monitor fluid flow and fluid condition variables either independently or simultaneously, as desired.

According to yet another object of the invention, the multi-functional apparatus may be selectively linked with a variety of external devices, including a rain gauge, a pump, and the like, utilizing suitable interface electronics integrally connected with the microprocessor of the apparatus. The apparatus is thus able to transmit control signals to the external device(s), and to receive and record data from same. The additional capabilities include, for example, the capability to automatically sample fluid on the basis of either fluid flow related variables or critical level(s) of fluid condition(s).

It is another object of the invention to substantially isolate fluid samples pertaining to a flow-related variable or to a fluid condition variable so as to substantially reduce laboratory analysis costs.

Another object of the invention is to provide a fluid flow monitoring apparatus which determines and reports average fluid velocity throughout a channel utilizing Doppler technology.

The above and further objects, details, and advantages of the invention will become apparent from the following detailed description, when read in conjunction with the accompanying drawings.

BRIEF DESCRIPTION OF THE DRAWINGS

FIGS. 20-30 are schematic diagrams of a preferred embodiment of the average fluid velocity computation unit of the present invention.

DETAILED DESCRIPTION OF PREFERRED EMBODIMENTS

Figure 32:
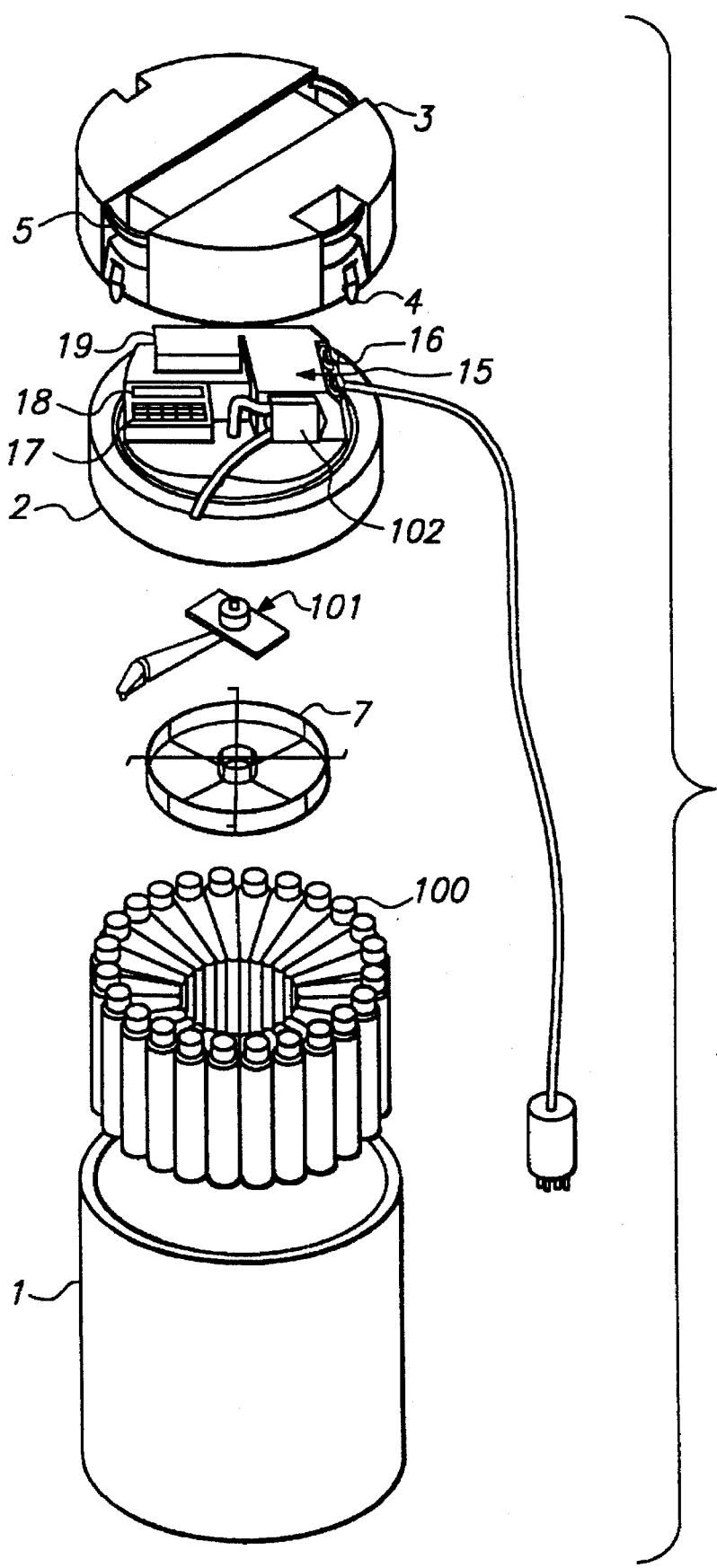
FIG. 32 is an exploded perspective view of a preferred embodiment of the present invention showing an automatic sampling unit assembly thereof.

With reference to FIGS. 1-4, there is shown a preferred embodiment of the multifunction flow monitoring apparatus according to the invention. The apparatus includes a compact case 1 which houses the various electronic, microprocessing, and mechanical components of the invention. Case 1 is preferably fabricated of a rugged thermoplastic material, such as ABS plastic, which is impact resistant and capable of withstanding the stresses of mounting and use under harsh conditions. The front portion of case 1 includes an operating panel 2 provided with a sealed membrane switch numeric keypad 3 for user input, a liquid crystal graphics/alphanumeric display 4, push buttons 5 for selectively operating display 4, and ON/OFF switches. A door 6, fabricated of a rugged thermoplastic material which is transparent, protectively covers the operating panel 2 when it is not being used. Door 6 is hingedly secured at 6A to one side of the front case portion, and is retained in a closed position by a pair of stainless steel lockable latches 6B at the opposite side. The case 1 including operating panel 2 is completely sealed so as to be watertight, with added protection of operating panel 2 being afforded by fastening door 6 in a closed position. However, even when door 6 is open, the case 1 with the components mounted therein is submersible, watertight, dust-tight, and corrosion resistant, conforming to NEMA 4X, 6 standards. In an alternative embodiment, case 1 is integrally formed with a housing for performing additional operations, such as performing fluid sampling operations, as shown in FIG. 32.

Figure 1:
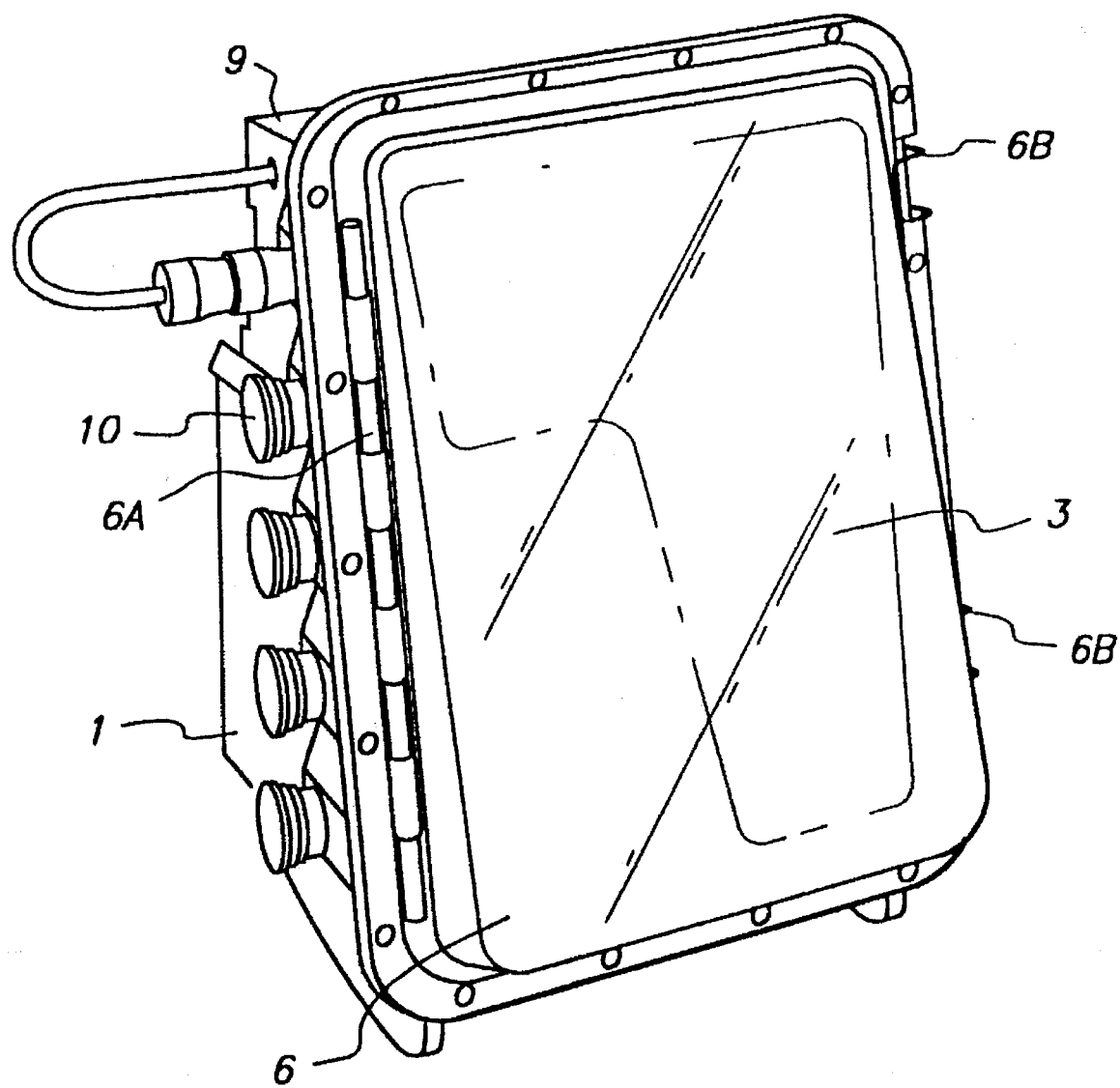
FIG. 1 is a perspective view of a multi-function flow monitoring apparatus according to a preferred embodiment of the invention.
Figure 2:
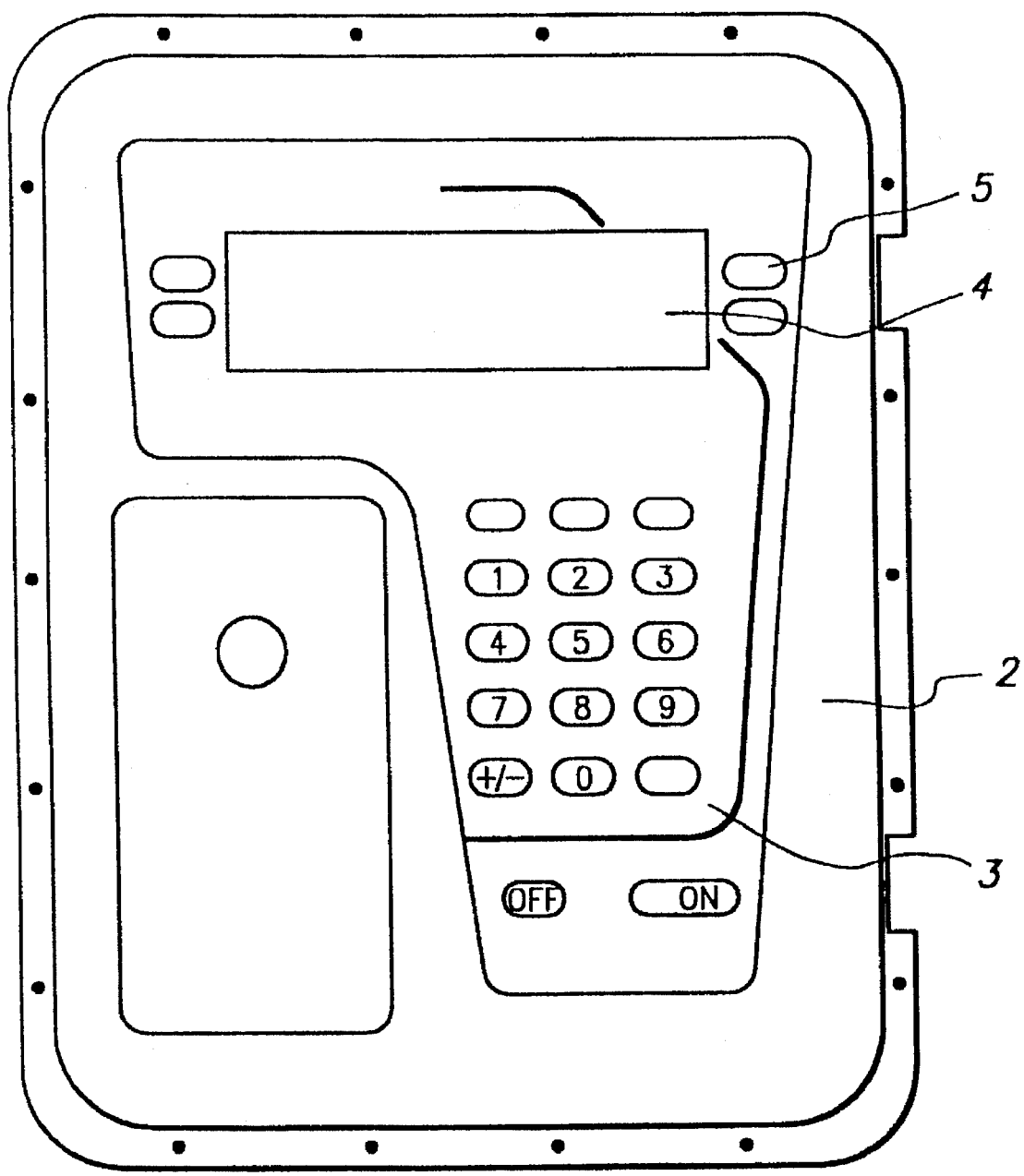
FIG. 2 is a front view of the operating panel of the apparatus of FIG. 1.
Figure 3:
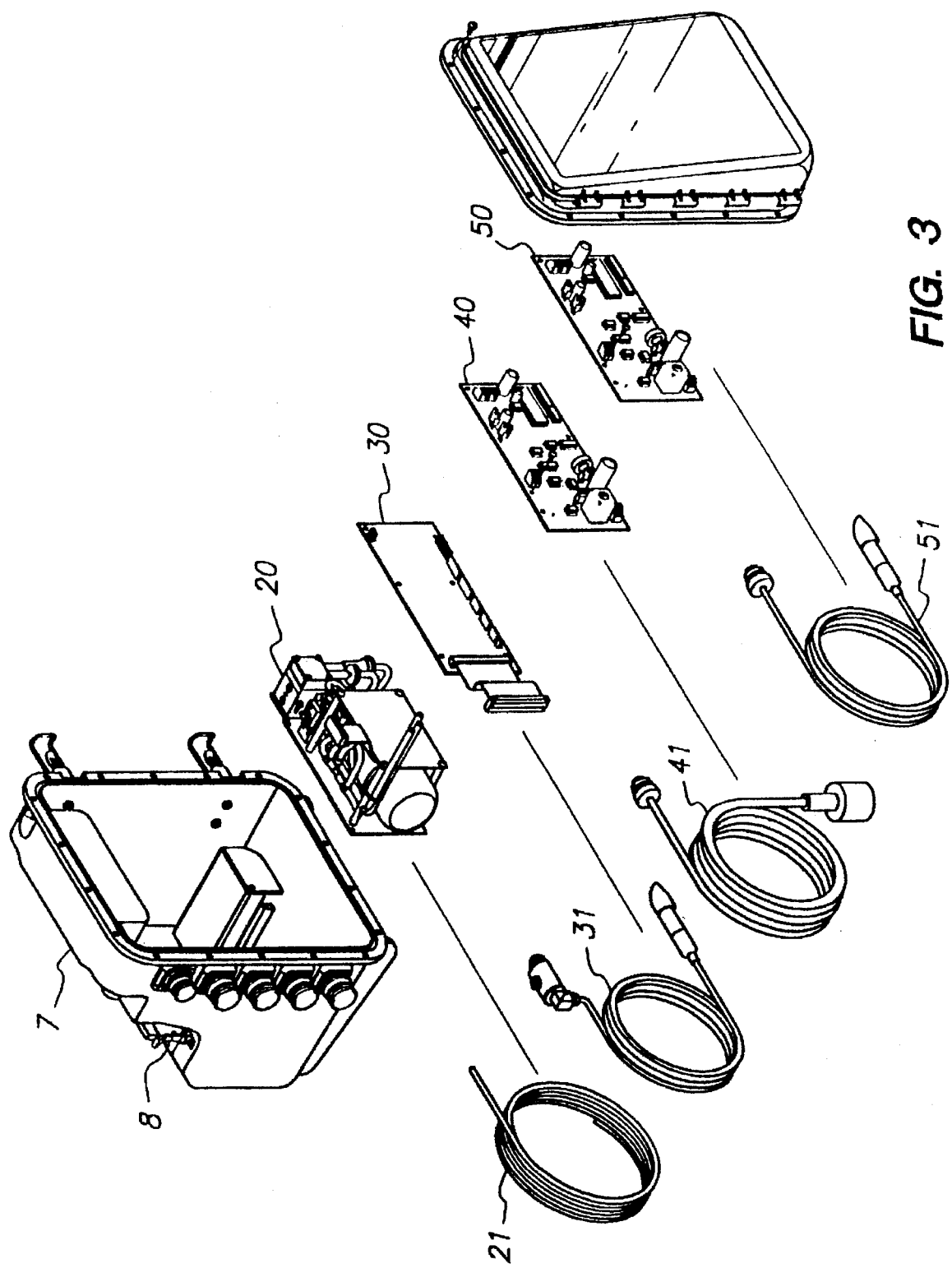
FIG. 3 is a partially disassembled view of the multi-function flow monitoring apparatus of FIG. 1, showing four interchangeable flow sensors accommodated by the apparatus together with their respective control modules.

As shown in FIG. 3, the rear top portion of case 1 may be provided with an integrally molded handle portion 7. Below the handle portion is an integrally molded recessed pocket portion 8 adapted to securely hold a power source for the apparatus, such as a battery 9, an A/C power converter, or the like.

Mounted on a side portion of case 1 is a plurality of external connectors 10 which preferably are each provided with a removable cap to protect same when not in use, although the connectors 10 are sealed in a watertight manner even without the caps. As described in greater detail below, connectors 10 are adapted to have various devices connected thereto, including any one of a plurality of interchangeable flow sensors, fluid condition monitoring sensor(s), a power source such as a battery, a data transfer unit, etc. It will be understood in this respect that the number of connectors 10 may be varied as desired to accommodate a desired number and/or types of sensors and external devices. In the embodiment shown in FIGS. 1–3, the uppermost connector 10 is adapted to receive one end of an electrical connector for connection to rear-mounted battery 9, which in a preferred embodiment provides a power source for the apparatus.

A principal feature of the multi-function fluid flow monitoring apparatus of the invention is its ability to calculate fluid flow-related variables on the basis of outputs from any one of a plurality of interchangeable flow sensors. In effect, the multiple flow sensor capability of the invention renders the apparatus equivalent to a plurality of different types of flow meters all integrated in a single unit. The user is thus able to adapt the apparatus for use in a wide variety of different site conditions simply by selecting a type of flow sensor which is suitable for the conditions at a given monitoring site, instead of having to switch to an entirely different flow meter. In the preferred embodiment described below, the apparatus is adapted to measure fluid flow-related variables on the basis of outputs from at least four different types of sensors, i.e., a bubbler-type pressure sensor, an ultrasonic type sensor, a submerged type sensor, and a velocity sensor forming part of an area-velocity sensor system. It will be understood, however, that the apparatus is capable of accommodating additional and alternative types of sensors by means of suitable control modules which may be integrally connected with the computer control means of the apparatus as desired.

Figure 5:
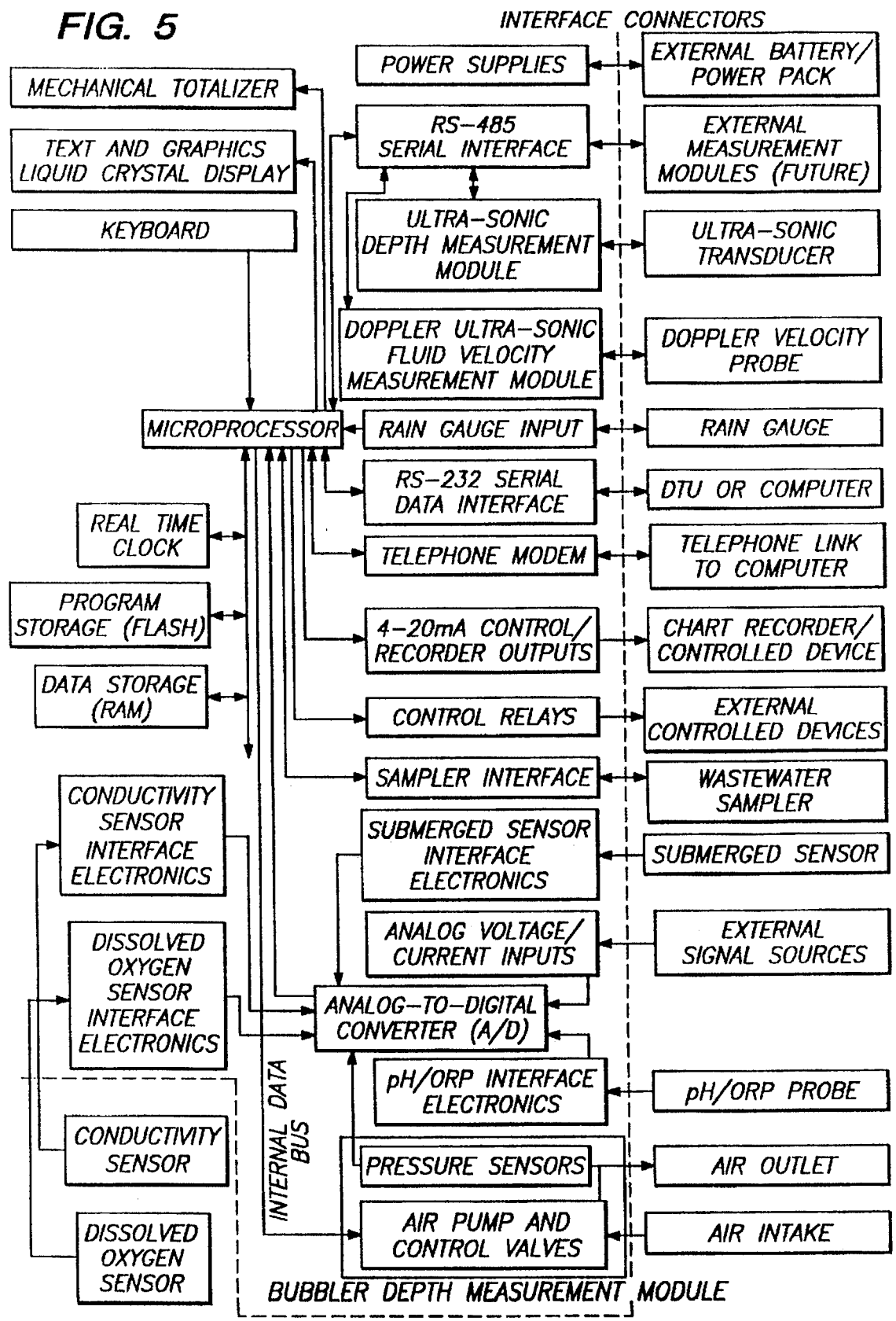
FIG. 5 is a block diagram of the various components of a preferred embodiment of the invention, as controlled by the computer control means of the apparatus.

As shown in FIG. 5, the apparatus according to the invention includes computer control means in the form of a microprocessor which performs all mathematical and control functions required to operate the apparatus, a keyboard (keypad 3 in FIG. 1) defining the interface to the user which allows the user to program the apparatus and monitor its operation, and a real-time clock. The real-time clock provides the computer control means with access to current time and date information, so that events occurring during program execution may be recorded with corresponding time and date of occurrence.

As shown in FIG. 3, four control modules 20, 30, 40, 50 are provided for the four interchangeable flow sensors 21, 31, 41, 51, respectively, with each module being integrally connected with the microprocessor within case 1 in the assembled state. Control module 20, which operatively cooperates with a bubbler type sensor in the form of bubbler tubing 21, includes an air pump and various mechanical and electronic circuitry components, including signal processing means, of a bubbler depth measurement system described in detail below. Control module 30, in the form of an electronic circuitry board, includes signal processing means and interface means for submerged sensor 31 as described in detail below. Likewise, control modules 40 and 50, each in the form of an electronic circuitry board, define signal processing and interface means for ultrasonic sensor 41 and a velocity sensor 51, respectively, as also described in detail below.

Submerged Sensor

With reference to FIGS. 1–3, 5 and 6, the operating characteristics of the invention will first be described with respect to sensor 31, which comprises a submerged pressure transducer.

By way of example, submerged pressure transducer or submerged sensor 31 is suitable for use in monitoring conditions where floating oil, grease, foam, steam, silt, solids, or turbulence are present. The sensor 31 is selectively connected with one of the connectors 10 on case 1, which is in turn connected with the microprocessor of the apparatus via control module 30. The interface means incorporated in module 30 are defined by signal conditioning electronics and an analog to digital ("A/D") converter, as represented in the lower portion of FIG. 5 by labelled blocks. The circuitry provided in control module 30 operates to transmit a precision voltage level to the sensor 31, as well as to condition and convert signals detected from sensor 31 for input to the computer control means. The detected signals are amplified and smoothed (filtered for noise), and then converted to digital form by an A/D converter (FIG. 5) for input to the microprocessor.

Figure 6:
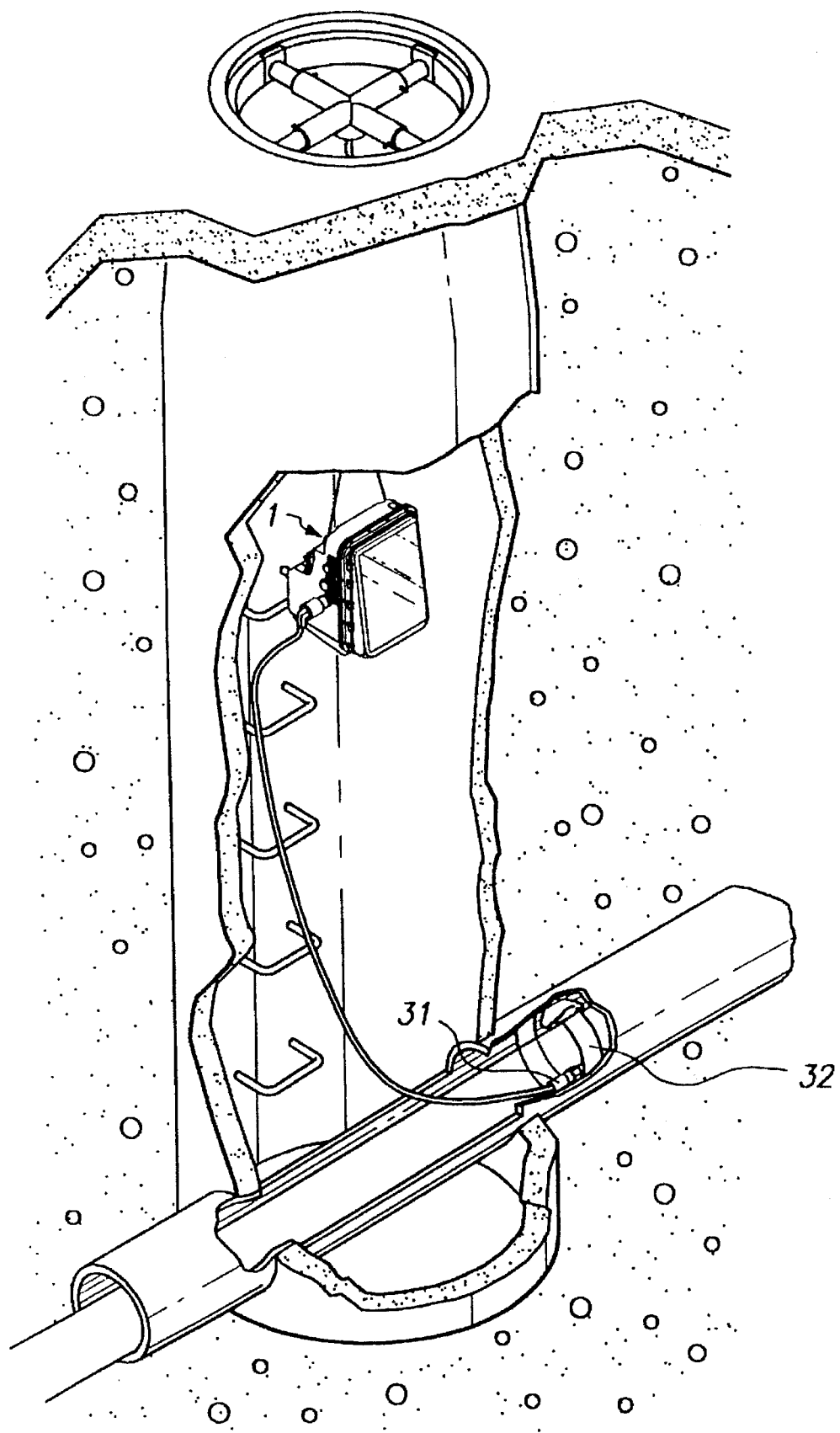
FIG. 6 is a perspective view of the apparatus according to the invention having a submerged sensor connected thereto, shown in a mounted position within a sewer manhole.

With reference to FIG. 6, the apparatus with submerged sensor 31 connected thereto is shown in a mounted position in a sewer manhole. As shown, the apparatus may be suspended by a plurality of lines attached to case 1 and extending from a cross-bar support provided at the upper end of the manhole. Sensor 31 is shown as installed in an open flowing sewer passage, secured in position by a stainless steel mounting band 32 such that the sensor is positioned directly in the flow stream. The pressure over the sensor 31 changes with changes in fluid level. The microprocessor of the apparatus, on the basis of inputs from sensor 31 processed by control module 30, converts the level reading to a flow rate based on the level-to-flow relationship of the channel configuration. The flow rate relationship is determined on the basis of the dimension, declination, and inside roughness of the pipe.

Submerged sensor 31, like the other interchangeable sensors described in detail below, may alternatively be installed in a fluid flow restricting or primary device which is in turn installed in an open flowing sewer passage to define a fluid channel for measuring fluid flow rate. Such a primary device may take the form of a weir, such as a V-notch weir, a contracted or non-contracted rectangular weir, a Cipolletti weir, a Thelmar weir, or a compound V-notch and rectangular weir. Alternatively, the primary device may comprise a flume, such as an H, HL or HS flume; a Parshall flume; a trapezoidal flume; a Palmer-Bowlus flume, or a Leopold-Lagco flume. The primary device may also take the form of a nozzle, such as a Kennison or parabolic nozzle.

Each of the foregoing primary devices is adapted to restrict fluid flow in an open passage so as to increase the fluid depth upstream of the device. The upstream fluid depth or "head" of each such device has a known mathematical relationship with the rate of flow through the channel of the device. This head vs. flow rate relationship is available in published form for various different sizes of each type of device.

When the sensor 31 is submerged upstream of one of the above-described flow restriction or primary devices, the voltage output from sensor 31 will be directly related to the "head" value used to calculate the flow rate. Typically, the sensor 31 will be mounted at a low point in a primary device so that it will remain submerged. Processing of the signals from sensor 31 and calculation of the flow rate is performed by the apparatus including the computer control means as described below.

The computer control means according to the invention comprises a microprocessor, and preferably has program storage firmware in the form of FLASH memory which permits software enhancements without replacing E-PROM chips. In addition to program storage memory, the computer control means is also provided with data storage memory in the form of random access memory (RAM) which stores specific details of operation set by the user and records flow and other data as described below. The RAM is backed-up by its own battery, e.g., a lithium battery, so that data will remain stored therein even when the overall power source of the apparatus is turned off.

Program Storage Memory.

The program storage memory of the computer control means according to the invention implements all of the functions required to read and process data from submerged sensor 31, as well as any other interchangeable sensor being used, and to operate the text and graphics display 4 and keypad 3. The program storage memory may include the following programming:

Interface Programming;

Flow Measuring Programming; and

Fluid Condition Monitoring Programming.

The Interface Programming allows the microprocessor to control the user input keypad 3, the text/graphics display 4, the real-time clock, and to access the active interface devices including the interchangeable sensors and any external devices connected with the apparatus. With respect to the bubbler module 20, the computer control means is also programmed to control operation of the bubbler air pump based on inputs from pressure sensors received via an A/D converter (FIG. 5), as described in greater detail below.

The Flow Measuring Programming allows the microprocessor to calculate the fluid depth, flow rate, velocity, and other fluid flow-related variables on the basis of processed signals received from the sensor 31 or one of the other interchangeable sensors described below. The programming includes depth vs. flow equations which characterize the relationship between the "head" and flow rate for various types and sizes of fluid flow restricting devices. Also included are equations (e.g., the Manning Equation) for calculating flow variables on the basis of sensor inputs directly from various shaped channels, such as round pipes, U channels, rectangular channels, and trapezoidal channels. While these various equations could alternatively be selectively input by the user via keypad 3, in the preferred embodiment of the invention the equations are stored in the program memory of the computer control system of the apparatus. Floating point math algorithms are provided to enable the microprocessor to perform high precision mathematical operations required to accurately calculate the values of fluid flow-related variables. Such fluid flow-related variables include the fluid depth which is calculated from the output of a selected one of the sensors, and the fluid flow rate which is calculated from the measured fluid depth. Algorithms are included for performing addition, subtraction, multiplication, division, exponentiations, logarithms and trigonometry functions to a precision equivalent to over four significant figures.

It will be understood that the Interface Programming and Flow Measuring Programming also allow the microprocessor to perform a variety of other operations which will become apparent from the following detailed description. For example, one such operation comprises a totalizer feature in which the microprocessor calculates and keeps a running total of the fluid quantity discharged over a given time period, on the basis of inputs from a flow sensor being used with the apparatus, with the running total being displayed on display 4. A second running total may also be provided which is re-settable by the user so as to track total flow over only a selected period of time. As shown in FIG. 5, a mechanical totalizer operated by the microprocessor is also provided so as to ensure that a totalized value will not be erased.

The Fluid Condition Monitoring Programming comprises firmware which allows the microprocessor to calculate the values of a given fluid condition(s) on the basis of processed signals received from a fluid condition sensor via suitable interface means, as described in greater detail below.

Data Storage Memory

The data storage memory of the computer control means is preferably provided in the form of random access memory (RAM) which stores specific operational parameters set by the user, and stores data during operation. Parameters which may be set by the user include fluid flow and fluid level logging intervals, such as on the basis of time, a given depth in the fluid channel, and/or rainfall (where a rain gauge is connected with the apparatus), as well as selection of a primary device or channel configuration. The user may also select parameters for monitoring fluid conditions such as pH, temperature, ORP, rainfall, conductivity, dissolved oxygen, turbidity, etc., on the basis of inputs from external signal sources as described below. Other parameters which may be set include control parameters such as trip points based on high and/or low fluid condition levels (e.g., pH levels or water level), which trigger the operation of an automatic sampling unit, a pump, or the like. A variety of other parameters which may be input by the user will become apparent from the description below.

The invention contemplates that the computer control means be programmed to selectively prompt the user, via a series of menu screens displayed on display 4, to enter various desired parameters via keypad 3. Various user-keyed parameters associated with particular sensors and devices are described in detail below. In addition to user-programmed entries, all data collected during operation is stored in RAM.

Bubbler Sensor

In accordance with the interchangeable flow sensor capability of the invention, the use of the apparatus as a bubbler-type pressure sensor system including the bubbler sensor 21 (FIG. 3) will now be described with reference to FIGS. 3–5 and 7–10.

The bubbler sensor 21, which comprises a length of plastic tubing, is particularly suitable for use in low or intermittent flow conditions, or where interfering conditions are present, such as floating oil, grease, foam, steam, surface turbulence, and/or excessive wind. Because only inexpensive tubing is exposed once the bubbler type sensor is mounted for operation, it is also well suited for applications in which vandalism may be a problem. The ease of installation of the bubbler sensor, described below, also makes it well suited for temporary flow applications, such as POTW monitoring or infiltration and inflow studies.

As shown in FIG. 3, the control module 20 for bubbler sensor 21 includes an air pump and various mechanical and electronic circuitry components of a bubbler depth measurement system according to the invention, including signal processing and interface means connected with the microprocessor. The bubbler system of the invention represents a substantial improvement over a conventional bubbler depth measurement system, such as shown in FIG. 8, as described in detail below.

Figure 8:
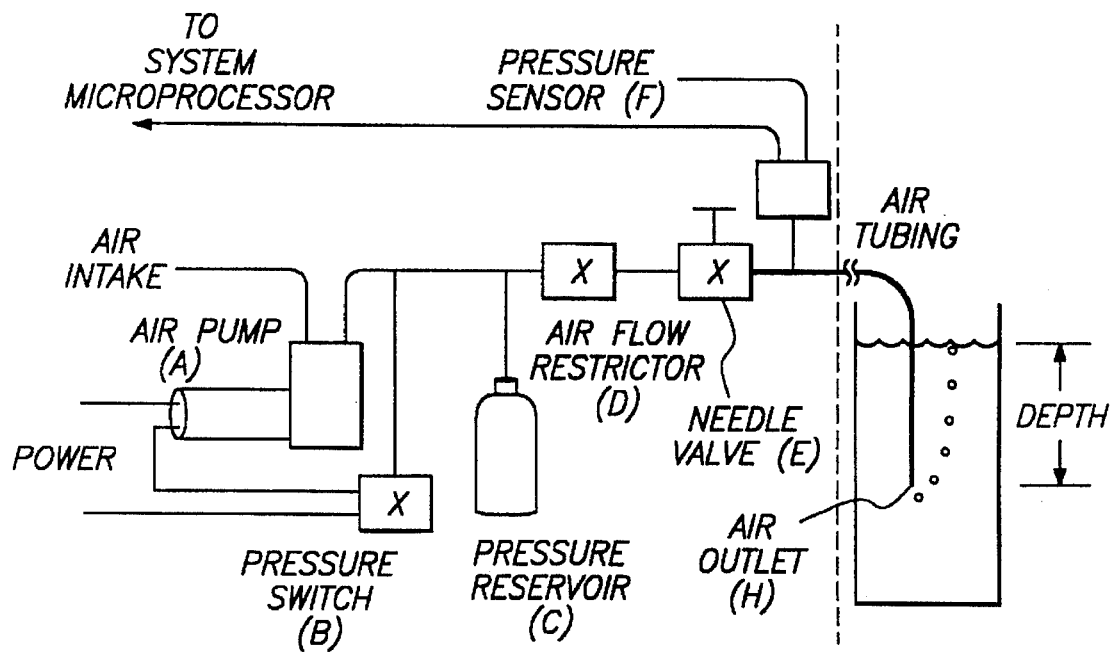
FIG. 8 is a diagrammatic view of a prior art bubbler flow sensor system.

With reference to FIG. 8, the conventional bubbler system includes an air pump A which is controlled by a pressure switch B so as to maintain an approximately constant air pressure in a pressure reservoir C. Such pressure must be sufficient to force air bubbles into the maximum fluid depth which is expected to be encountered by the system, as follows:

$$P \geq 0.03612 \times D$$

where

P=Reservoir Pressure (PSI)

D=Maximum expected water depth (inches)

In the conventional system, an air flow restrictor D and needle valve E cooperate to limit the air flow from the reservoir to some desired rate. In practice, the user adjusts the needle valve to obtain an air flow rate which yields approximately one to three bubbles per second from the air outlet H. Air outlet H is mechanically fixed in place inside a fluid channel. The fluid depth in the channel may then be determined by measuring the back pressure on the output air line by means of a pressure sensor F. Ideally, the fluid depth may be calculated as:

$$D = 27.681 \times P$$

where

D=Channel fluid depth (inches)

P=Measured Pressure (PSI).

In reality, however, the movement of air through the output tubing adds a friction term to the measured pressure. This friction or error term must be subtracted from the measured pressure in order to make an accurate depth calculation, as follows:

$$D = 27.681 \times [P - f(l,d,v)]$$

where

D=Channel fluid depth (inches)

P=Measured Pressure f(l,d,v)=Measured Pressure Error due to air moving in output tube; a function of air tubing length (l), diameter (d), and air flow velocity (v).

The magnitude of the error term is determined by the length and diameter of the output tube, and the velocity of the air flowing through it. Two of the factors in the error term, the tubing length (l) and diameter (d), remain constant for a given installation. However, the air flow velocity is primarily a function of the position of the needle valve, and the pressure difference between the pressure reservoir and the air output. Because the air outlet is mechanically fixed inside the fluid channel, this pressure difference will be determined primarily by the fluid depth in the channel. The net result is that the fluid depth calculated by the conventional system will include an error term which is a function of the current needle valve setting, the length and diameter of the output tubing, and the current depth in the fluid channel.

When the conventional system shown in FIG. 8 is used in applications where the measured fluid depth changes only slightly, the error term [f(l,d,v)] is more or less constant, and may be compensated for when installing and calibrating the system at the site. When the conventional system is used in applications where the fluid level varies over a wide range, the error term will add significantly to worst case measurement error. In either case, any movement of the needle valve after calibration will alter the error term and thus detrimentally affect the accuracy of depth measurement.

Another problem which the conventional bubbler system of FIG. 8 suffers is excessive power consumption. When the system is adjusted to provide a suitable bubble rate at maximum fluid depth, the air flow will be substantially greater near zero fluid depth. This causes the air pump to run more frequently, thus consuming additional power. Such power consumption is particularly undesirable in battery operated systems where battery life is an important factor.

Figure 9:
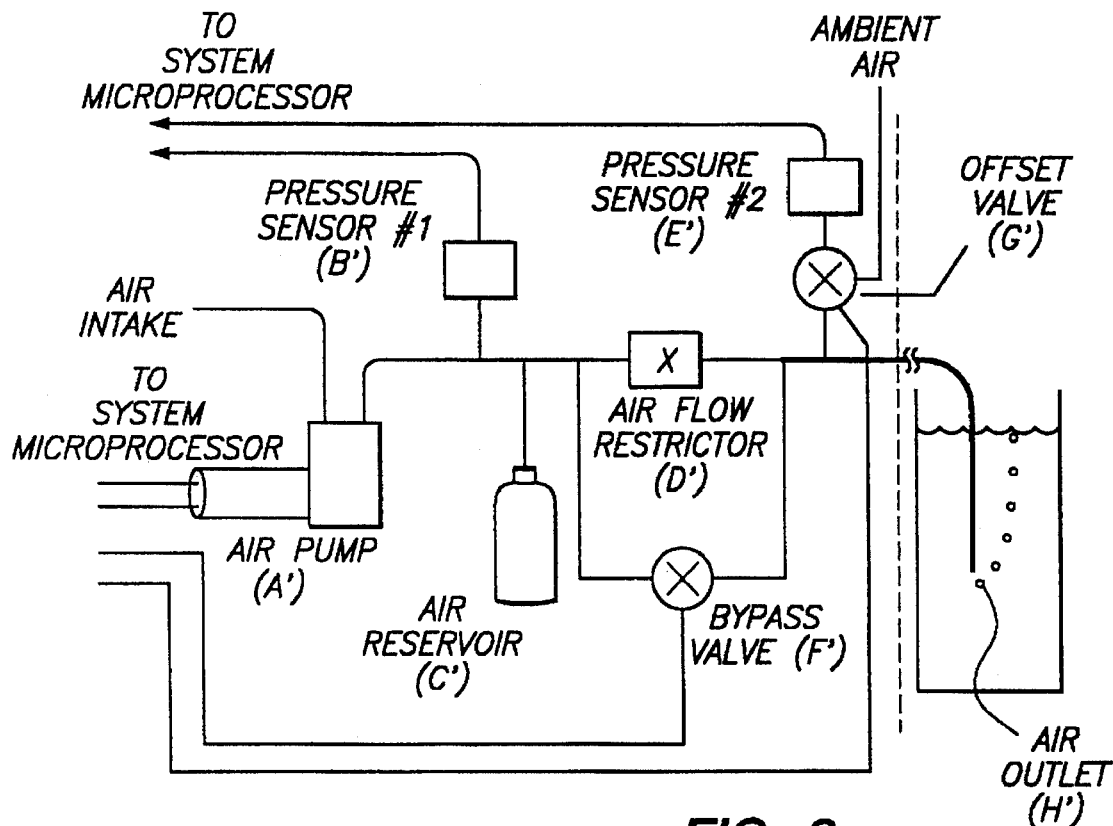
FIG. 9 is a diagrammatic view of a bubbler flow sensor system according to the invention, as incorporated within the multi-function flow monitoring apparatus.
Figure 10:
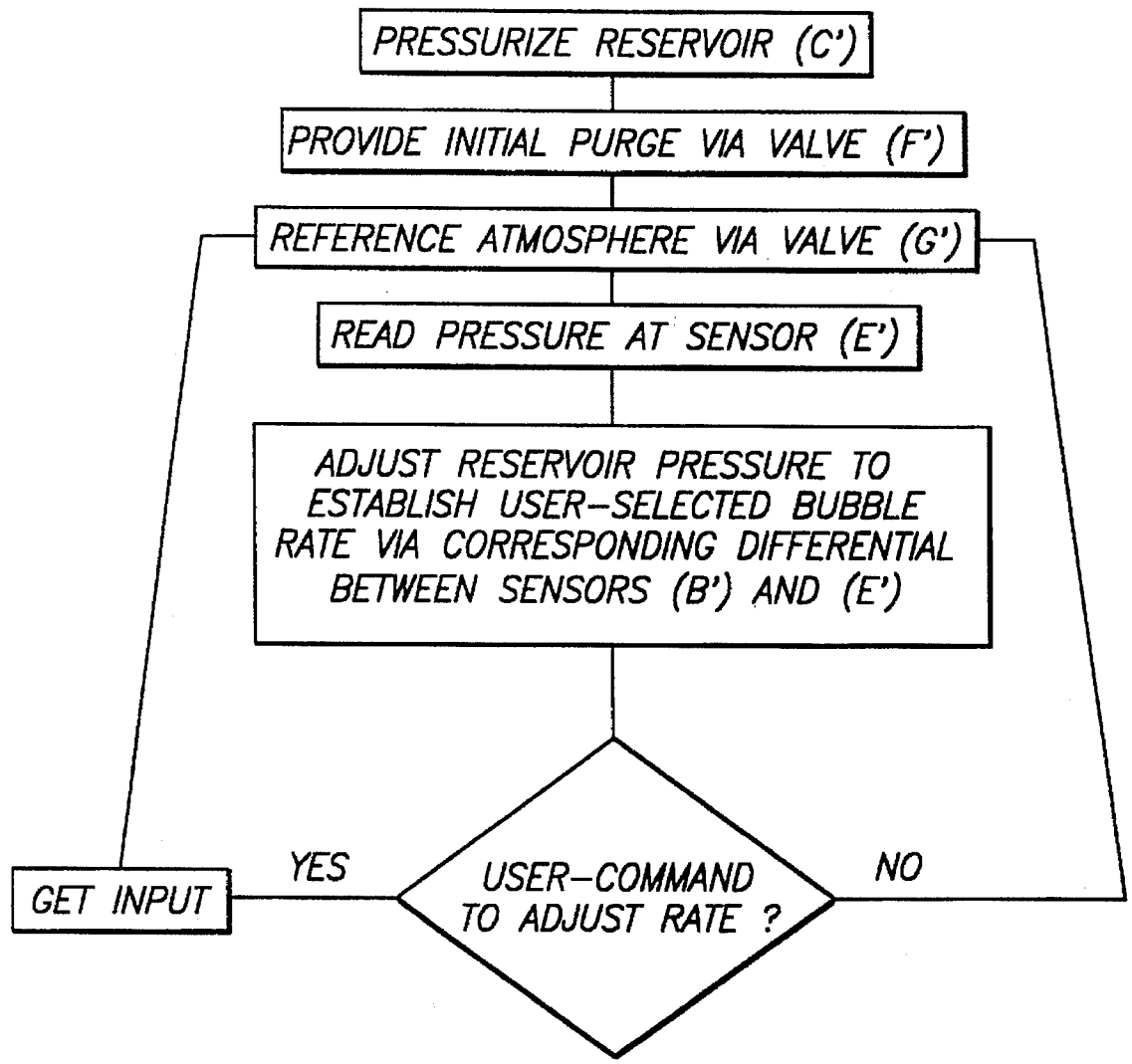
FIG. 10 is a flow chart showing operational sequences of the bubbler flow sensor system of the invention.

The bubbler system according to the present invention, shown in the block diagram of FIG. 9, overcomes the various problems associated with the conventional bubbler system of FIG. 8 while maximizing accuracy and minimizing power consumption. The bubbler system according to the invention includes an air pump A' which pressurizes an air reservoir C', both of which are housed, together with other components of the bubbler system, within case 1 of the apparatus as part of the bubbler control module 20 (FIG. 3). Unlike the conventional system, in the bubbler system according to the invention the air pump A' is controlled by the microprocessor of the apparatus. The microprocessor is programmed to determine when and for how long the air pump A' must be run by reading the two pressure sensors B' and E' shown in FIG. 9. As shown in FIG. 5, inputs from pressure sensors B' and E' are transmitted to the microprocessor via an A/D converter. The pressure difference between sensors B' and E' is equivalent to the pressure drop across the air flow restrictor D'. The microprocessor controls operation of pump A' so as to maintain a predetermined pressure across the air flow restrictor D'. As the fluid level in the channel changes, the pressure maintained in the reservoir C' is thus changed by a like amount.

An important advantage afforded by the bubbler system according to the invention is that the constant pressure across the air flow restrictor D' results in a nearly constant air flow or bubble rate into the fluid channel, thus virtually eliminating the depth dependency from the error term in the depth-pressure equations set out above for the conventional system. The depth-pressure relationship for the bubbler system according to the invention is as follows:

$$D = 27.681 \times [P - f(l,d)]$$

where

D=Channel depth (inches)

P=Pressure measured at pressure sensor E' (PSI)

f(l,d)=Measured Pressure Error due to air moving in output tube; a function of air tubing length (l) and diameter (d).

Because the bubbler system according to the invention effectively controls the air flow velocity, it is unaffected by the fluid depth in the channel. The tubing-based error term (f(l,d)) from which the conventional system suffers, while still present, is in the present system a function of only the output air tubing length and diameter. The error term is thus constant for a given installation and may be effectively canceled at the time the apparatus of the invention is installed and calibrated at the site.

Another important advantage afforded by the bubbler system according to the invention is that a lower pressure is maintained in the air reservoir C' when the channel fluid depth is less than the maximum. The lower reservoir pressure reduces pump run time, thus conserving power and increasing battery life. A further advantage of the present system is that the air flow or bubble rate is set by a command to the microprocessor of the apparatus which is effected via keypad 3, rather than mechanical adjustment of a needle valve as in the conventional system. Once the bubble rate has been initially set by the user, it will remain constant even when the apparatus is moved from one installation site to another. In most cases, the bubble rate need never be changed from the original factory setting for the life of the unit.

Figure 4:
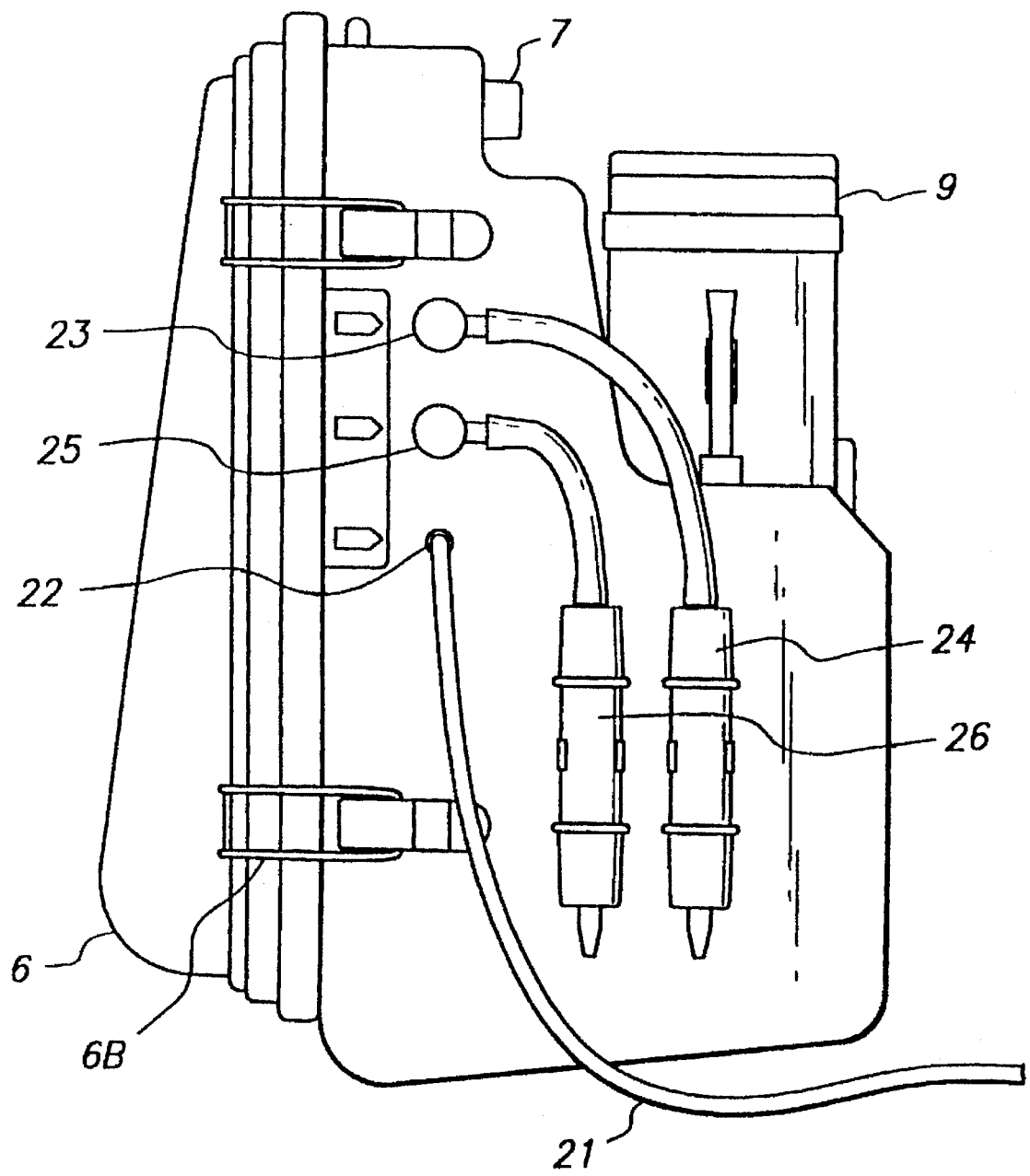
FIG. 4 is a side view of the apparatus of FIG. 1, showing externally mounted components forming part of the bubbler sensor system of the apparatus.

As shown in FIG. 4, the bubbler sensor tubing 21 is selectively connected to the apparatus via a bubbler line port connection 22 which is preferably provided on the side of case 1 opposite the side provided with connectors 10. Also provided is an air intake port 23 with an associated dryer tube 24 for air supply to the bubbler air pump A', as well as a reference port 25 with an associated dryer tube 26. The reference port 25 communicates with the atmosphere via an offset valve G' as shown in FIG. 9. The microprocessor is programmed to open the bubbler port and reference port to atmosphere at regular intervals, and to electronically zero same so as to eliminate any drift due to changing barometric pressure. Further, a bypass valve F' is opened periodically by the microprocessor for a short time. The resulting burst of high velocity air through the air tube helps to dislodge any debris which otherwise might accumulate on the air outlet H' and restrict air flow.

The sequential steps of initializing and operating the bubbler system, as described above, are summarized in the flow chart of FIG. 10.

Figure 7:
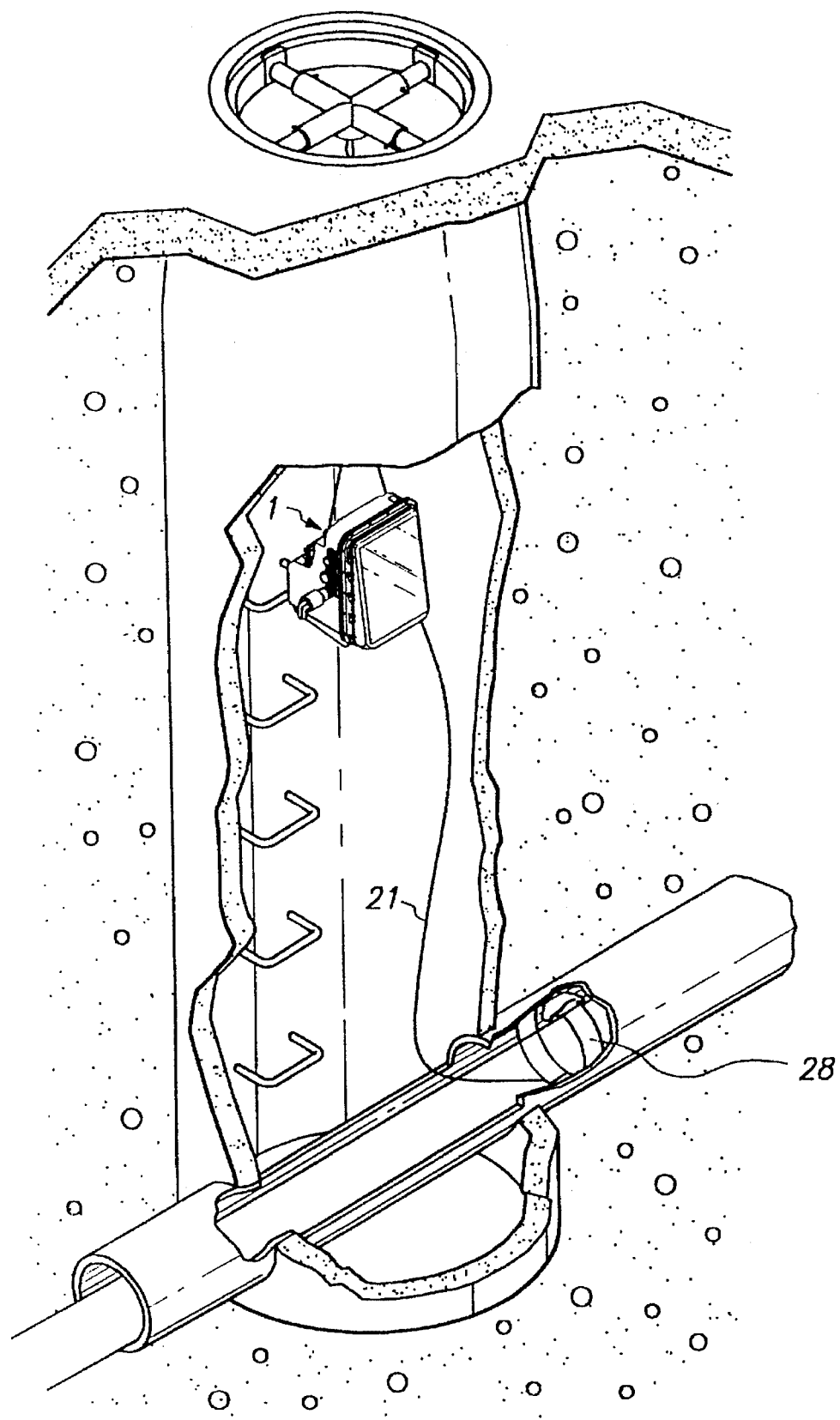
FIG. 7 is a perspective view of the apparatus according to the invention having a bubbler sensor connected thereto, shown in a mounted position within a sewer manhole.

With reference to FIGS. 4 and 7, installation and operation of the bubbler type sensor is as follows. The bubbler sensor 21 is connected at one end to bubbler line port connection 22 and is mounted at its other end within the fluid in a channel. As shown in FIG. 7, a stainless steel mounting band 28 may be used for securing the outlet end of sensor 21 in a channel, although it is contemplated that any suitable mounting means may be employed. The bubbler air supply arrangement described above, in cooperation with the microprocessor of the apparatus following the sequence of steps shown in FIG. 10, communicates through the bubbler line port 22 with bubbler sensor 21 so as to direct a constant, small volume of air through the tubing of sensor 21 to the measurement point in the fluid channel. As the pressure in the sensor tubing 21 changes in proportion to fluid level, the flow measuring programming converts the level reading to flow based on the level-to-flow relationship of the channel configuration, or that of a primary device.

In accordance with another embodiment of the invention, the bubbler sensor system as described above may alternatively be provided in a single-sensor capacity fluid flow monitoring apparatus or flow meter. Such embodiment would include the bubbler control module 20, but not the other control modules 30, 40 and 50 shown in FIG. 3. The bubbler type fluid flow monitoring apparatus as thus constructed may also include any one or more of the other multi-functional features of the invention, such as the ability to link the apparatus with external devices such as a rain gauge, automatic fluid sampling apparatus, and the like, as well as accommodating one or more fluid condition monitoring sensors.

Ultrasonic Sensor

Figure 11:
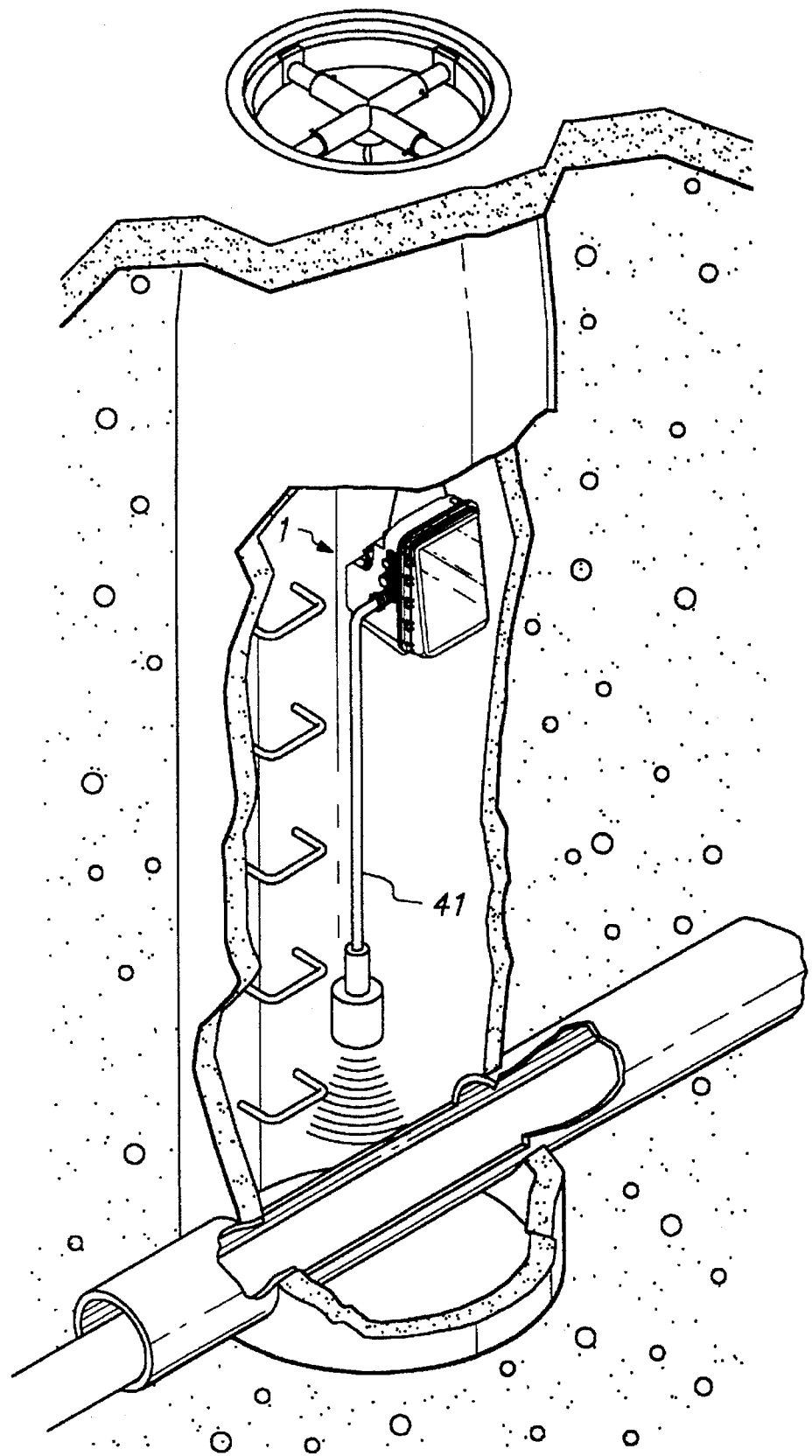
FIG. 11 is a perspective view of the apparatus according to the invention having an ultrasonic flow sensor connected thereto, shown in a mounted position within a sewer manhole.

In accordance with the interchangeable flow sensor capability of the invention, the use of the apparatus with the ultrasonic type sensor 41 (FIG. 3) will now be described with reference to FIGS. 3, 5 and 11.

The ultrasonic transducer or sensor 41, which functions without contacting the fluid being monitored as discussed below, is particularly suitable for use where chemicals would adversely affect a sensor located in the fluid. The ultrasonic sensor 41 is also suitable for permanent applications, particularly where silt or solids are present. Further, because ultrasonic sensor 41 is mounted above the fluid channel instead of within the channel, it is capable of accurately measuring channel depth as low as zero and is not affected by high fluid velocities in the channel.

The signal processing and interface electronics for sensor 41 are provided on control module or board 40 as shown in FIG. 3. Ultrasonic sensor 41 uses an echo range measurement through air technique to measure the distance from a fixed point above the channel to the fluid surface. The output from sensor 41 based on such measurement, processed by control module 40 for input to the microprocessor, is then processed to calculate the depth of the fluid in the channel, and the rate of flow. Control module 40 cooperates with sensor 41 to supply a series of acoustic pulses from a high-energy, high-frequency source which are directed toward the fluid surface by sensor 41, and echo signals are reflected back and processed in order to calculate values such as average fluid flow rate, as described below.

The operating parameters of the ultrasonic sensor system as described above are all controlled by the microprocessor of the apparatus, with which control module 40 is connected. The microprocessor performs routine optimizing operations to determine and adjust the optimal settings for pulse strength, pulse width, detector sensitivity, and frequency. For example, if the echo signal quality deteriorates below an acceptable level, the condition will be detected and automatically corrected. Because the frequency at which the ultrasonic sensor 41 is driven can be varied, while the strength of the resulting echo is monitored, the ultrasonic sensor system according to the invention effectively tunes itself to match the particular ultrasonic sensor being used. The user is thus able to replace one ultrasonic sensor with another in the field, without having to return the unit to the factory for re-tuning.

In use, ultrasonic sensor 41 is selectively connected to one of the connectors 10 on case 1 which is in turn connected with ultrasonic control module 40. As shown in FIG. 11, the apparatus with the sensor 41 connected thereto is installed in a sewer manhole in the manner described above with respect to the other types of sensors. As also shown in FIG. 11, the sensor 41 is positioned above the fluid in the channel, which may be accomplished by simply allowing the sensor cable to hang from the connector 10. It will be understood, however, that any suitable mounting means may be used for mounting sensor 41, provided that the sensor is held in position above the fluid and out of contact therewith.

Area-Velocity Sensor System

In accordance with the interchangeable flow sensor capability of the invention, the use of the apparatus as an area-velocity sensor system (FIG. 3) will now be described with reference to FIGS. 12–14 and 20–30.

The area-velocity sensor system according to the invention includes a fluid level measuring subsystem and a fluid velocity measurement subsystem. The fluid level measuring subsystem may take the form of any of the above-described flow sensor systems capable of measuring fluid depth, including the bubbler sensor system, the ultrasonic sensor system, or the submerged sensor system described above. The fluid velocity measurement subsystem, used in conjunction with the fluid level measuring subsystem, includes the velocity sensor 51 and associated electronic circuitry provided on control module or board 50, with module 50 being connected with the microprocessor of the apparatus. The circuitry details of module 50 are shown diagrammatically in FIG. 14, and discussed in detail below. When it is desired to use the velocity sensor 51, its coaxial cable is selectively connected with the apparatus via one of the connectors 10 which is in turn connected with module 50. Simultaneously, one of the flow sensors 21, 31, or 41 is connected with its associated connector 10, so as to measure fluid level.

Figure 12:
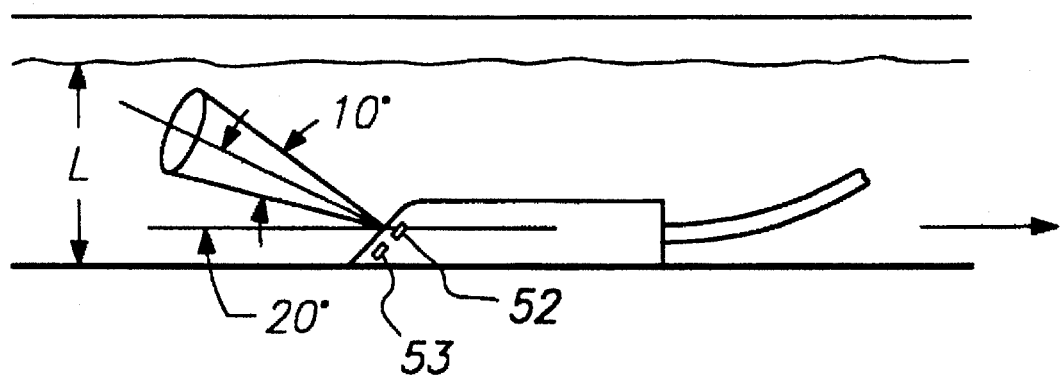
FIG. 12 is a side elevational view of a velocity sensor forming part of an area-velocity sensor system according to the invention, as mounted in an open fluid channel.

The velocity sensor 51 is shown in FIG. 12 as mounted on the bottom of an open channel, with fluid flowing through the channel to the right as indicated by the arrow. Sensor 51 is mounted substantially horizontally, facing in the upstream direction so as to eliminate sensor induced turbulence on the velocity measurement. It will be understood with respect to the following description of velocity measurement that free surface, open channel flow is assumed. To simultaneously measure fluid level, designated as L in FIG. 12, one of the sensors 21, 31, 41, or an alternative flow sensor capable of measuring fluid depth, is also mounted in the channel.

Provided within the plastic housing of sensor 51 is a piezoelectric transmit transducer 52 and a piezoelectric receive transducer 53. The signal processing circuitry on board 50 of the apparatus transmits average velocity results to the microprocessor while simultaneously the microprocessor receives fluid level information from the fluid level measuring subsystem. The microprocessor then calculates average flow rate by the following equation:

Average Flow Rate=Average Velocity×Channel Cross-Sectional Area

The channel cross-sectional area is calculated by the microprocessor on the basis of channel geometry information entered by the user via keypad 3, and fluid level information.

The fluid velocity subsystem of the area-velocity sensor system operates on the principle of the Doppler frequency shift of a transmitted electromagnetic wave. A high frequency (e.g., 1-Megahertz) ultrasonic wave is emitted from transmit transducer 52 at an angle from the long axis of the sensor (typically an angle of 15° to 35°, e.g., 20° in FIG. 12), with the wave being emitted in the form of a cone with a 10° cone angle as shown in FIG. 12. Relative motion between the stationary probe and moving particles in the fluid are detected by receive transducer 53, which is manifested as a change in frequency from the transmitted wave. This Doppler shifted frequency is proportional to the speed of the moving particles in the fluid.

Figure 14:
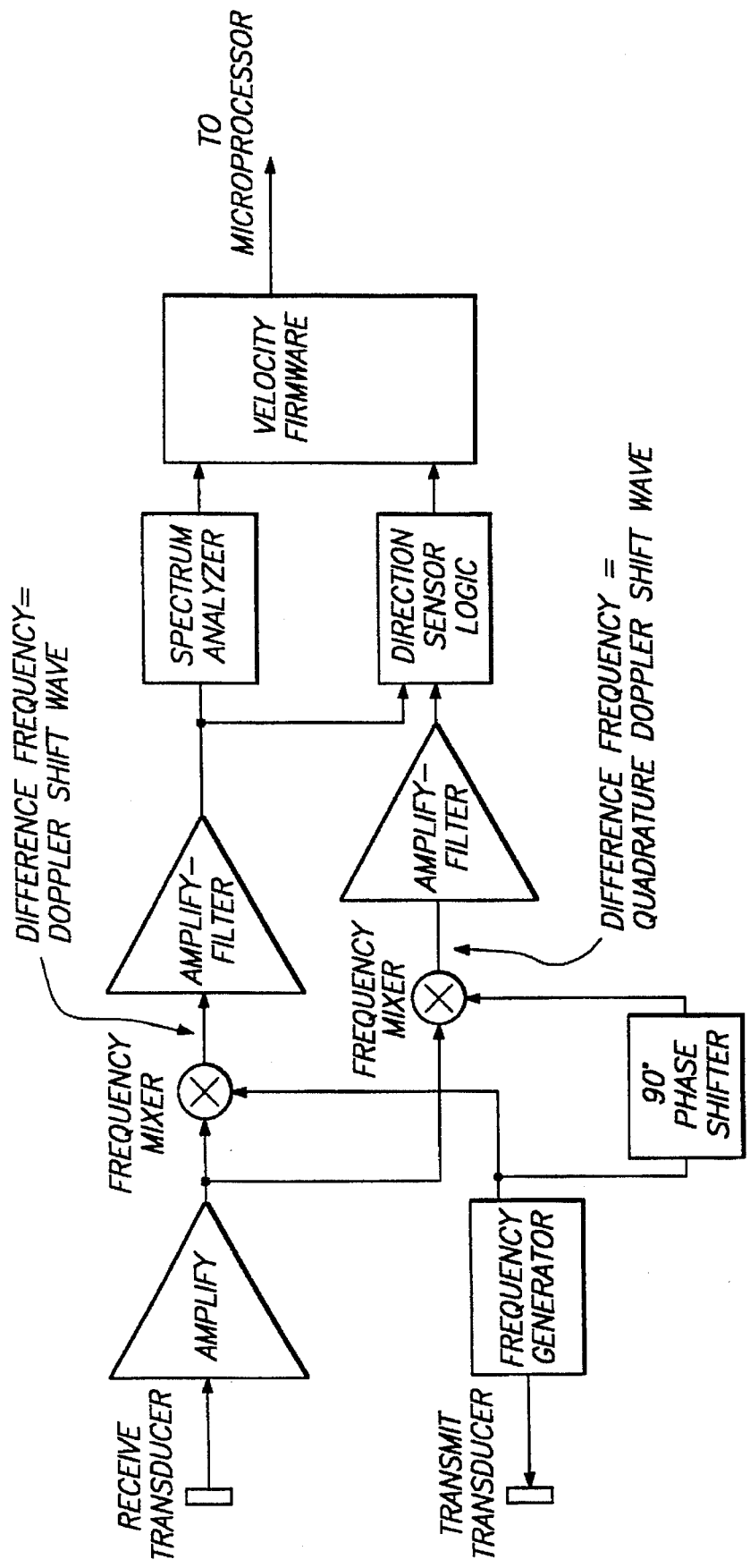
FIG. 14 is a block diagram showing the processing circuit for signals received from the velocity sensor of FIG. 12.

The signal from receive transducer 53 actually comprises a time domain sum of sinusoidal signals corresponding to packets of scattering particles in the fluid. As shown in FIG. 14, circuitry provided on control module 50 processes the signal from receive transducer 53 by amplifying, filtering, and mixing it with the transmitter frequency, yielding the sum and difference frequencies of the inputs to the mixer.

Figure 13:
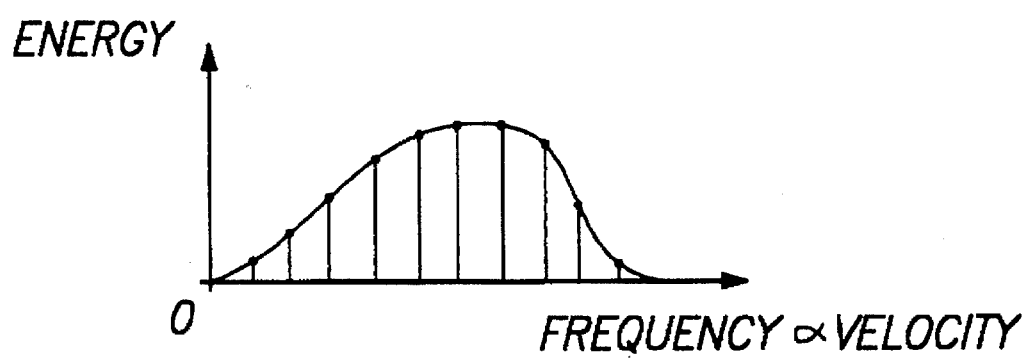
FIG. 13 shows a typical frequency distribution of signals from the velocity sensor of FIG. 12.

The sum frequency is filtered out and the difference frequency is the actual Doppler shifted frequency. This Doppler signal is then input to a spectrum analyzer circuit on module 50, and a frequency scan is performed on the time domain signal over the expected full-scale range of velocities for the instrument. The output comprises a weighted frequency distribution of the input signal over discrete, evenly-spaced frequency intervals, as shown in FIG. 13. The weighting of each frequency component corresponds to the strength of the scattered energy at each velocity interval. To obtain average velocity, the centroid of this frequency distribution is calculated and the result is used by the microprocessor for calculating the average flow rate.

The flow direction, whether downstream or upstream, is obtained by detecting the relative phase difference between the actual transmitted wave and the quadrature shifted (90°) transmit wave. This quadrature transmit wave is processed internally on module or board 50 in parallel with the actual transmitted wave to yield the actual Doppler wave and a quadrature shifted Doppler wave. The quadrature shifted Doppler wave is used only for flow direction sensing, and not in the average velocity measurement. The actual Doppler wave and the quadrature shifted Doppler wave are then input into direction sensing firmware which assigns a direction to the velocity before it is transmitted to the microprocessor.

Referring to FIGS. 20–30, there is shown the circuit diagrams depicting the area-velocity sensor system according to the preferred embodiments of the present invention. Clock generator circuit 79 (FIG. 29) generates in-phase and quadrature phase clock signals running at a relatively high frequency, such as 1 MHz. Transmitter circuit 70 (FIG. 22) accepts the in-phase clock signal and transmits the clock signal throughout the channel. The transmitted signal is reflected by particles within the fluid and the reflected (or echo) signal is received by receiver 71 (FIG. 20) and amplified therein. The echo signal comprises a time domain sum of sinusoidal signals corresponding to packets of scattering particles in the fluid, and possesses a change in frequency from the original transmitted signal. This frequency change is the Doppler frequency shift, which is related to the velocity of the objects from which the signals are reflected.

The output of receiver circuit 71 is accepted by in-phase audio channel 72 (FIG. 23) as well as by quadrature-phase audio channel 76 (FIG. 21). In-phase audio channel 72 receives the amplified reflected signal and mixes it with the in-phase clock using mixer circuit 72A so as to yield a signal having the sum and difference frequencies thereof. The component of the output signal representing the difference in frequencies between the reflected signal and the in-phase clock is the frequency shifted Doppler component.

Low-pass filter 72B receives the output from mixer circuit 72A and is tuned so as to select the component thereof representing the difference in frequencies between the reflected signal and the in-phase clock, which comprises the frequency shifted doppler signal in the audio band. An AGC amplifier 73 (FIG. 24) maintains the amplified doppler signal within an acceptable amplitude range, comprising a rectifier circuit followed by an integrator amplifier. Similarly, quadrature phase audio channel 76 receives the amplified echo signal and mixes it with the quadrature phase clock using mixing circuit 76A, and low-pass filter 76B passes the quadrature-shifted doppler signal.

The doppler signal from the in-phase audio channel 72 is then amplified by two-stage amplifier 72C, 72D, the output of which drives spectrum analyzer 77 (FIG. 27). Spectrum analyzer 77 is preferably but not necessarily a swept tuned local oscillator comprising a frequency generator having voltage controlled oscillator (VCO) 77F which generates an oscillating signal whose frequency is microprocessor-controlled; mixer circuit 77B, which mixes the VCO 77F output signal with the doppler signal; bandpass filter 77A which accepts mixer circuit 77B output and passes a narrow band of frequencies centered at a predetermined intermediate frequency; and peak detector 77C which receives the output of filter 77A and generates an output representative of the peak energy level thereof. The output of peak detector 77C is then digitized (FIG. 28) for storage in digital memory 78B (FIG. 30). In this way, microprocessor 78A (FIG. 30) can be programmed to step the voltage control input of VCO 77F so that VCO 77F is swept across the desired frequency range in predetermined increments. The energy level of the doppler signal at each desired frequency can thereby be sequentially extracted by being passed through IF filter 77A, detected by peak detector 77C and then digitized and stored in memory 78B together with its corresponding frequency, so that a frequency distribution of the doppler signal over discrete, substantially spaced intervals is substantially obtained. In one preferred embodiment of the present invention, the energy levels of the doppler signal are extracted at substantially evenly-spaced frequency intervals.

By way of one example, filter 77A is a 4th-order high Q bandpass filter centered at 10 kHz and having a 3 dB bandwidth of 46 Hz; and microprocessor 78A steps VCO 77F over approximately a 3.5 kHz frequency range between 10 kHz and 13.5 kHz so that doppler frequencies between 0 and 3.5 kHz are passed through IF filter 77A. These doppler frequencies correspond to fluid velocities between 0 and 10 ft/sec.

Once the frequency distribution of the doppler signal has been stored in memory 78B, microprocessor 78A computes the centroid thereof, which is approximately equal to average fluid velocity.

The area-velocity sensor system preferably but not necessarily includes a means for verifying the accuracy of the average fluid velocity as calculated by spectrum analyzer 77 and microprocessor 78. The verification means preferably but not necessarily calculates a maximum velocity of fluid flow substantially concurrently with the average flow rate calculation and compares the maximum value with the average value. If the calculated average fluid velocity is not at least a predetermined percentage of the calculated maximum fluid velocity value, then the calculated average velocity value is discarded and the calculated maximum velocity value is reported as the average velocity value, following multiplication thereof by a constant. By way of one example, the calculated average flow rate is discarded unless it is at least 72% of the calculated maximum velocity value, and the reported average velocity is 90% of the calculated maximum velocity value when the computed average velocity value is less than 72% thereof.

Specifically, the verification means preferably but not necessarily comprises comparator 74 (FIG. 25), which receives the doppler signal generated by amplifier 72D and converts the signal into a digital square wave so as to provide a digital representation of the doppler signal; direction comparator 75 (FIG. 26), which determines the direction of fluid flow by comparing the quadrature-phase mixed signal from audio channel 76 with the squared doppler signal from comparator 74 so as to yield the relative phase difference therebetween; timing circuitry within microprocessor 78A which accepts the output from comparator 74 as well as the in-phase clock, measures substantially consecutive time periods of the output from comparator 74, and stores the measured time values of consecutive time periods in memory; and arithmetic circuitry, also within microprocessor 78A, which sorts through a predetermined number of stored time periods, selects a predetermined number of the values therefrom representing the smallest time periods (i.e., those time periods corresponding to the highest frequency), obtains a sum of the smallest time periods and normalizes the sum. The normalized sum is then multiplied by a constant in order to convert maximum frequency to maximum velocity in to units of feet/second. This result is the calculated maximum fluid velocity value which is used to verify the legitimacy of the calculated average fluid velocity value.

By way of one example, 100 consecutive time periods are measured by the verification means, and the 27 smallest measured time periods thereof are summed and normalized in computing maximum fluid velocity.

Figure 15:
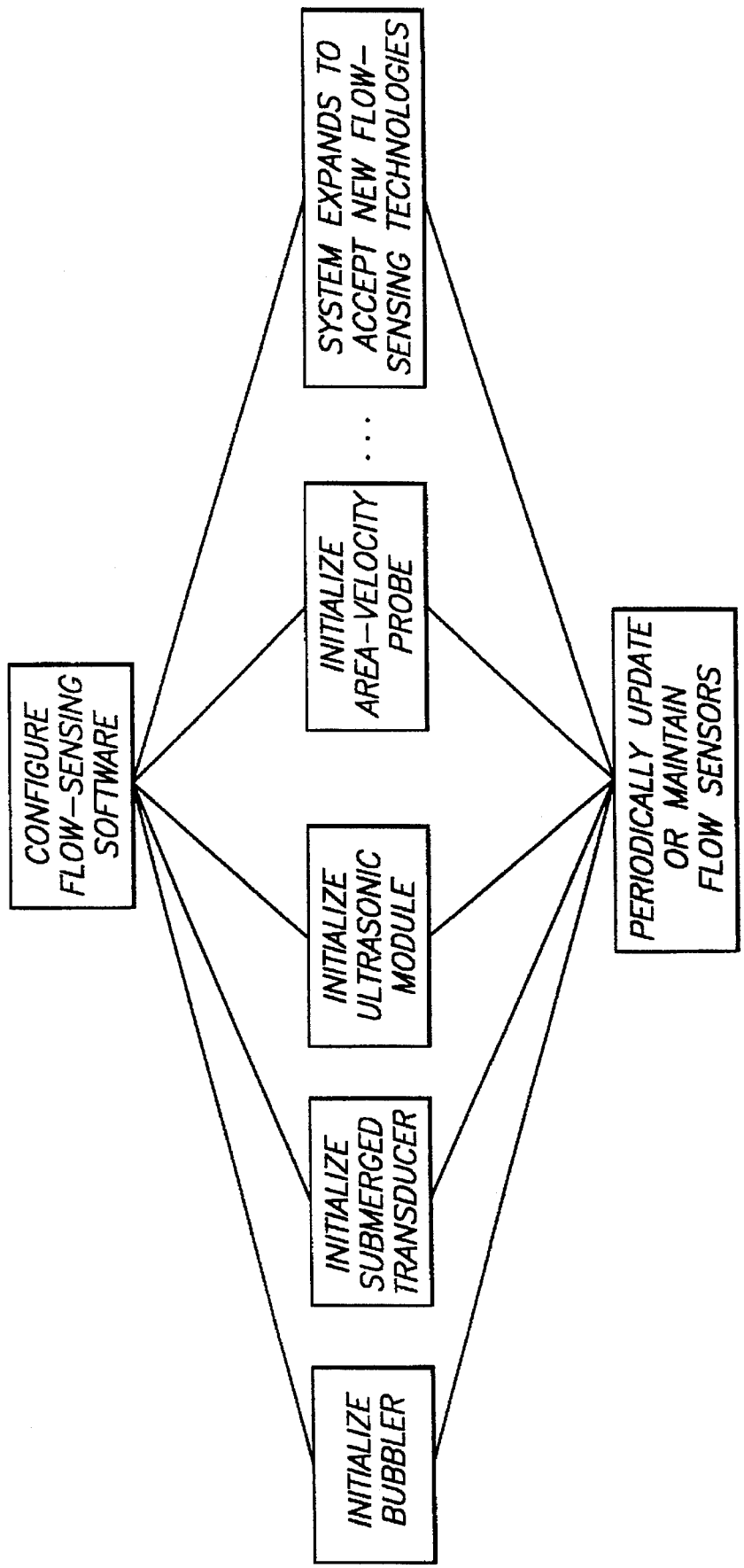
FIG. 15 is a flow chart showing operational sequences of the apparatus according to the invention.

With reference to FIG. 15, there is shown a flow chart showing the overall sequence of operation of the apparatus with respect to the four sensor systems described above. From FIG. 15 and the above detailed description of the four sensors 21, 31, 41, and 51, and their respective control modules 20, 30, 40, and 50, it will be understood that the flow monitoring apparatus of the invention essentially incorporates four different flow monitoring assemblies into a single compact unit. By employing a common microprocessor and command structure, and housing the computer control means with modules 20, 30, 40, and 50 in a single case, the apparatus is able to accommodate a very wide range of monitoring needs which heretofore could be accommodated only by relying upon a number of separate flow meter devices. The case 1 which houses the microprocessor and control modules of the invention is at least as compact as commercially available flow meters which are limited to use with only a single type of flow sensor. In order to adapt the operation of the apparatus to the desired bubbler, submerged sensor, ultrasonic sensor, or area-velocity mode, the user has merely to connect the desired sensor or sensors to the appropriate connector(s) 10 and enter corresponding operating parameters via keypad 3. The invention thus enables the user to select from a variety of flow sensor systems the particular type which will be best suited to a given monitoring application.

Multi-Functional Modes of Operation

In addition to the unique capability of the invention to selectively operate as essentially four (or more) different flow meters in accordance with the above-described embodiment of the invention, the apparatus of the invention may also be integrally provided with one or more means for monitoring various fluid conditions, such as pH, ORP, temperature, dissolved oxygen, conductivity, turbidity, and the like.

The means for monitoring a given fluid condition(s) preferably takes the form of one or more fluid condition monitoring assemblies or control modules such as those disclosed in the aforesaid U.S. Pat. No. 5,172,332, the disclosure of which is incorporated herein by reference thereto. Four such fluid condition monitoring assemblies or modules are depicted in the block diagrams of FIGS. 16–19, i.e., for a pH sensor, a conductivity sensor, an ORP sensor, and a dissolved oxygen sensor, respectively. FIGS. 16–19 are all partial system views showing only the individual fluid condition monitoring modules and electrode stations as connected to the microprocessor of the apparatus, with the various other components of the invention shown in FIG. 5, including the various control modules for the flow sensors, omitted for ease of illustration.

Figure 16:
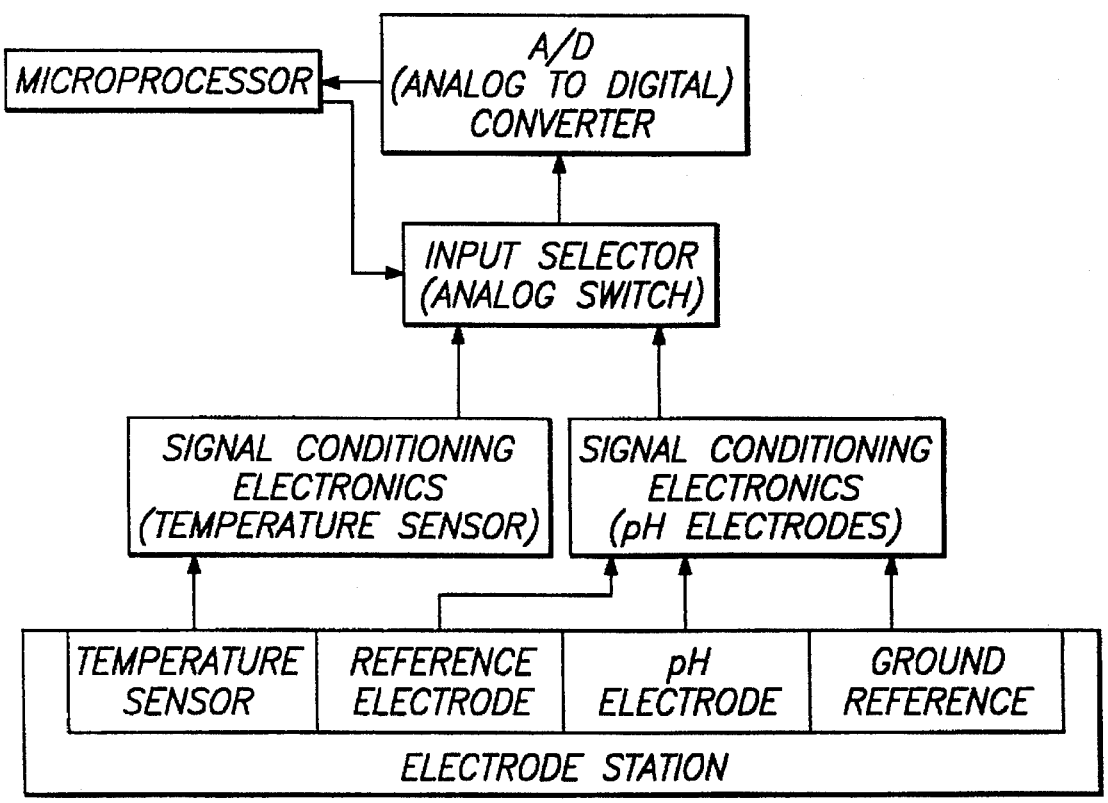
FIG. 16 is a partial block diagram showing a fluid condition monitoring assembly with an associated pH electrode station, with other system components omitted for ease of illustration.

It is contemplated that each of the fluid condition monitoring assemblies or control modules of FIGS. 16–19 may desirably be provided in the form of a single board similar to the control modules 30, 40, and 50 shown in FIG. 3. As shown in FIG. 16, a control module for a pH electrode station or sensor includes signal conditioning electronics, an input selector (analog switch), and an A/D converter. These components may be provided on a single board which is integrally connected with the microprocessor within case 1, and which is also connected to one of the external connectors 10. Programming in the form of firmware is provided which allows the microprocessor to calculate the pH level on the basis of processed signals received from the fluid condition monitoring assembly or module, and to record calculated data in RAM. Programming is also provided to permit calibration of the sensor, and to permit user selection, via keypad 3, of the time interval for recording data. A sensor in the form of a pH electrode station may be selectively connected to the corresponding connector 10, so that pH levels can be monitored along with fluid flow-related variables. A more detailed description of the structural and functional features of the pH sensor control module and the electrode station itself is set out in the aforesaid U.S. Pat. No. 5,172,332.

Figure 17:
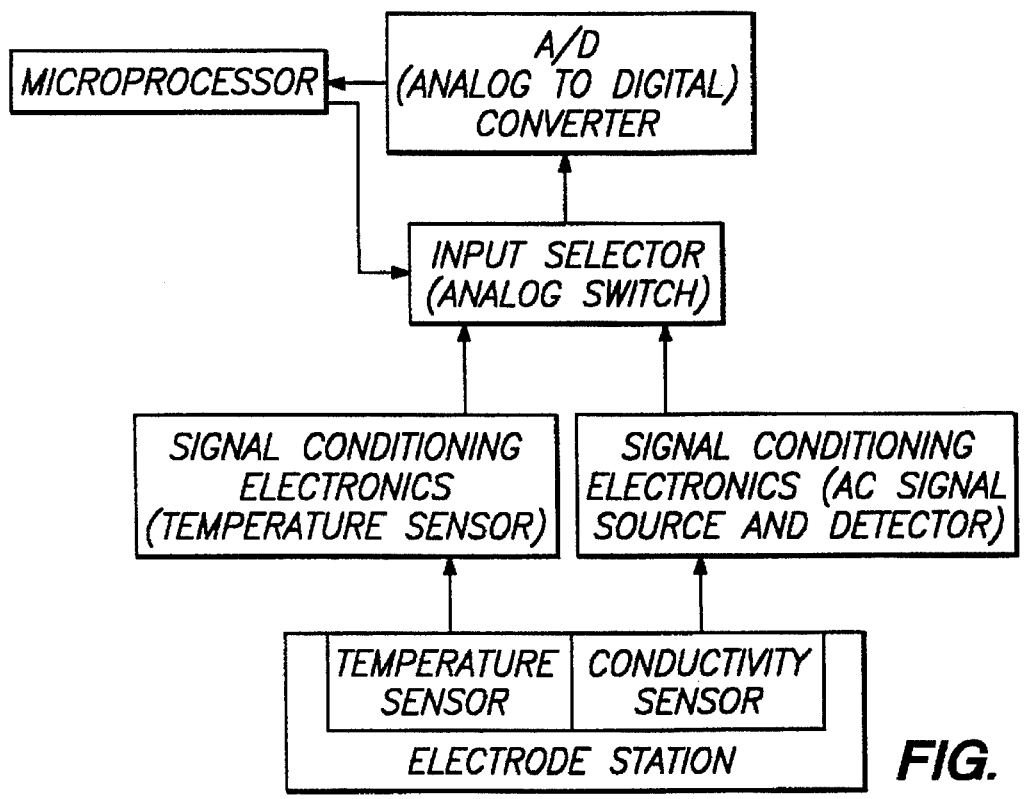
FIG. 17 is a partial block diagram showing a fluid condition monitoring assembly with an associated conductivity electrode station, with other system components omitted.

With reference to FIG. 17, a control module for a solution conductivity sensor includes signal conditioning electronics, an input selector (analog switch), and an A/D converter, all preferably provided on a single board connected with the microprocessor within case 1, and also connected to one of the external connectors 10. Programming in the form of firmware allows the microprocessor to calculate the conductivity level on the basis of processed signals received from the fluid condition monitoring module, and to record calculated data in RAM. Programming is also provided to permit calibration of the sensor, and user selection via keypad 3 of the time interval for recording data. A solution conductivity electrode station or sensor is selectively connected to the corresponding connector 10 to permit monitoring of conductivity levels. A more detailed description of the conductivity sensor control assembly or module and the electrode station itself is set out in the aforesaid U.S. Pat. No. 5,172,332.

Figure 18:
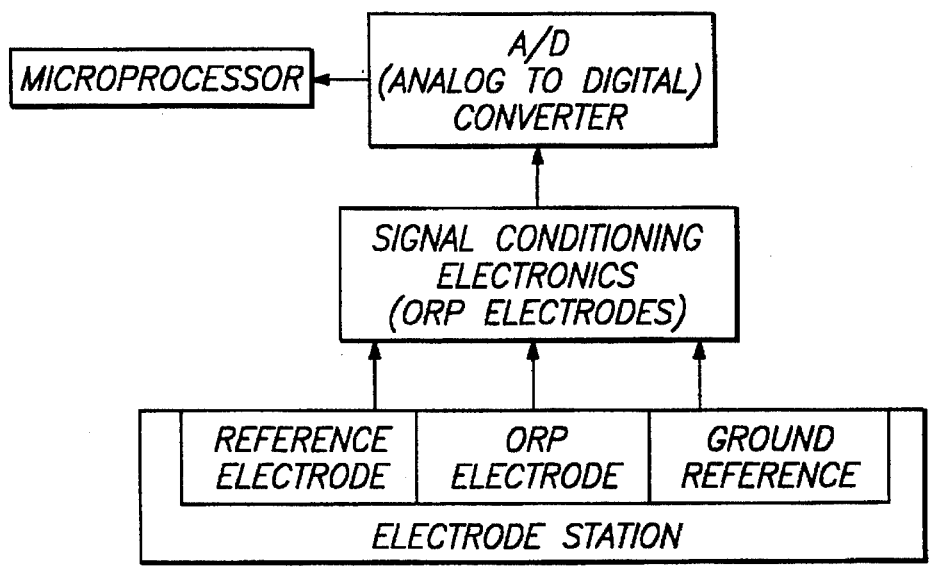
FIG. 18 is a partial block diagram showing a fluid condition monitoring assembly with an associated oxygen reduction potential ("ORP") electrode station, with other system components omitted.

FIG. 18 shows a control assembly or module for an oxygen reduction potential ("ORP") sensor, including signal conditioning electronics and an A/D converter preferably provided on a board connected with the microprocessor within case 1, and also connected to one of the external connectors 10. Programming in the form of firmware allows the microprocessor to calculate the ORP level on the basis of processed signals received from the fluid condition monitoring module, and to record calculated data in RAM. Programming is also provided to permit calibration of the sensor, and user selection via keypad 3 of the time interval for recording data. An ORP electrode station or sensor is selectively connected to the corresponding connector 10 for monitoring of ORP levels. A more detailed description of the ORP control assembly or module and ORP electrode station is set out in the aforesaid U.S. Pat. No. 5,172,332.

Figure 19:
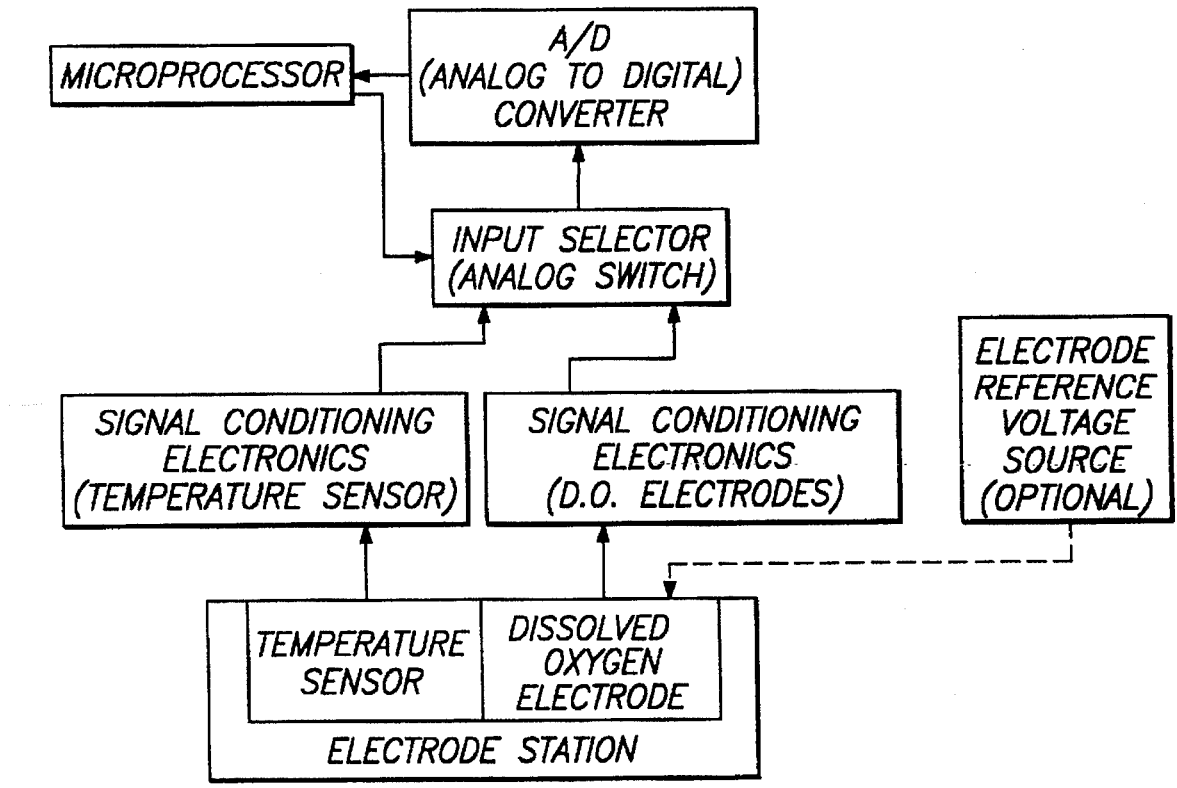
FIG. 19 is a partial block diagram showing a fluid condition monitoring assembly with an association dissolved oxygen electrode station, with other system components omitted.

With reference to FIG. 19, there is shown a control assembly or module for a dissolved oxygen sensor of either a polarographic or galvanic type. The control module includes signal conditioning electronics, an optional electrode reference voltage source, an input selector (analog switch), and an A/D converter. The control module circuitry is preferably provided on a board, which is connected with the microprocessor within case 1 and also connected to one of the external connectors 10. Programming in the form of firmware allows the microprocessor to calculate the dissolved oxygen level on the basis of processed signals received from the fluid condition monitoring assembly or module, and to record calculated data in RAM. Programming is also provided to permit calibration of the sensor, and user selection via keypad 3 of the time interval for recording data. A dissolved oxygen electrode station or sensor is selectively connected to the corresponding connector 10 for monitoring of dissolved oxygen levels. A more detailed description of the dissolved oxygen control assembly or module and dissolved oxygen electrode station is set out in the aforesaid U.S. Pat. No. 5,172,332.

By incorporating one or more of the fluid condition monitoring assemblies shown in FIGS. 16–19, the apparatus according to the invention may be adapted to monitor a number of different fluid conditions. To this end, the program storage memory of the computer control means of the apparatus may be programmed to perform the calculations necessary for a variety of different fluid conditions, and to allow for necessary calibration. As such, the program storage memory can be programmed to have a relatively universal capacity capable of processing inputs from a variety of different fluid condition sensors. It will be understood that the invention is not limited to the particular fluid conditions and sensors described above, and other suitable known sensors and corresponding interface electronics and programming may be employed for monitoring other conditions. With the multi-functional fluid monitoring and flow sensing capabilities of the invention, the user can choose to monitor and record data relating to a given fluid condition either independently of flow, or in conjunction with flow.

It will be further understood that the fluid flow monitoring apparatus of the invention may be selectively employed for use for flow monitoring only, for fluid condition monitoring only, or for monitoring both flow and fluid condition(s) simultaneously. These independent or dual operation modes can be effected by user input via keypad 3 to the microprocessor of the apparatus.

As shown in the diagram of FIG. 5, the multi-function fluid flow monitoring apparatus of the invention may also be capable of being linked with a variety of devices, such as an automatic sampling apparatus, a rain gauge, a pump, and the like. To this end, suitable interface electronics are provided, as shown in FIG. 5, which allow the microprocessor to operably communicate with the sampling apparatus, an external rain gauge, etc. The device interface electronics are in turn connected with the microprocessor of the apparatus, and suitable programming is provided to permit the apparatus to send control signals to the these device(s), as well as to receive and record data from same.

By way of example, the apparatus of the invention may be connected to an automatic sampler similar to that disclosed in the aforesaid U.S. Pat. Nos. 5,091,863 or 5,172,332. The user may then instruct the apparatus, via keypad 3, to initiate sampling operations by the automatic sampling unit on the basis of a fluid flow related variable, or on the basis of high, low, or a range of critical levels of fluid condition(s) as calculated by the microprocessor on the basis of inputs from one of the fluid condition monitoring modules.

The multi-function fluid flow monitoring apparatus according to the present invention may include a means for initiating a fluid sampling operation based upon at least one fluid parameter, and a means for substantially isolating one or more collected fluid samples from other collected samples. In this way, the present invention not only increases the likelihood of collecting an intermittent discharge containing a fluid flow related variable pertaining to an out-of-limit condition, but also substantially segregates the samples from other samples so as to reduce laboratory costs in analyzing numerous collected samples.

By way of one example, the apparatus collects fluid samples upon the detection of an out-of-limit condition pertaining to a first fluid variable, such as a flow related variable or a fluid condition variable, and stores the sample in a container into which samples pertaining to other fluid variables or to a timed sampling interval are prevented from being stored. Alternatively, a plurality of different fluid variables are monitored for collecting and storing fluid samples in separate isolated fluid reservoirs.

As shown in FIG. 32, the fluid collecting means preferably but not necessarily comprises fluid reservoirs 100; distributor mechanism 101, which is operably pivotal about a substantially lateral axis so as to direct collected fluid into the desired reservoir 100; and pump 102, which is operably connected to distributor mechanism 101 so as to draw fluid therein based upon control signals generated by the apparatus microprocessor. By way of one example, there are 24 reservoirs 100, one to four of which are dedicated for storing isolated fluid samples.

Figure 33A:
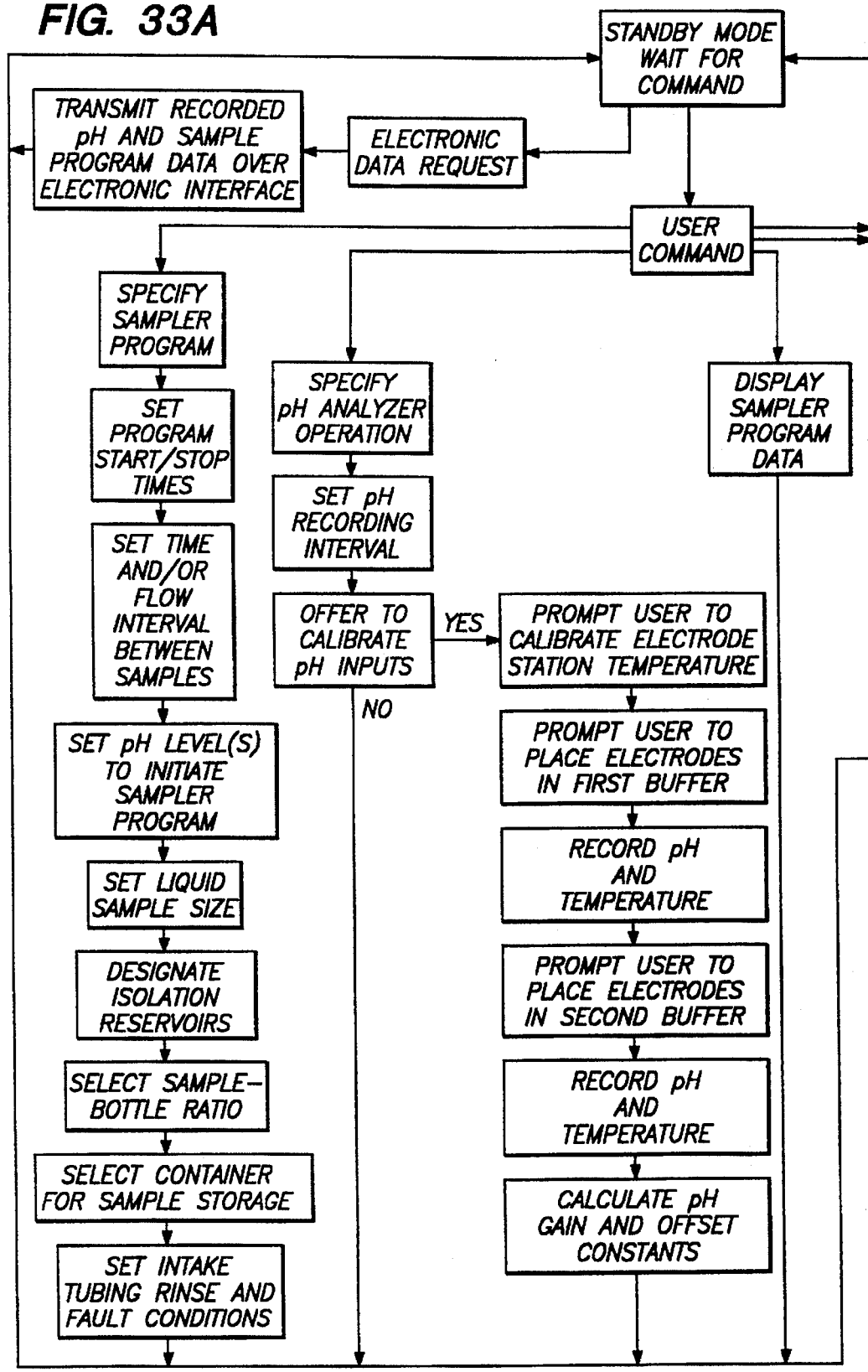
FIGS. 33A and 33B are flow charts showing operational sequences of the apparatus according to a preferred embodiment of the present invention.
Figures 33, 33B:
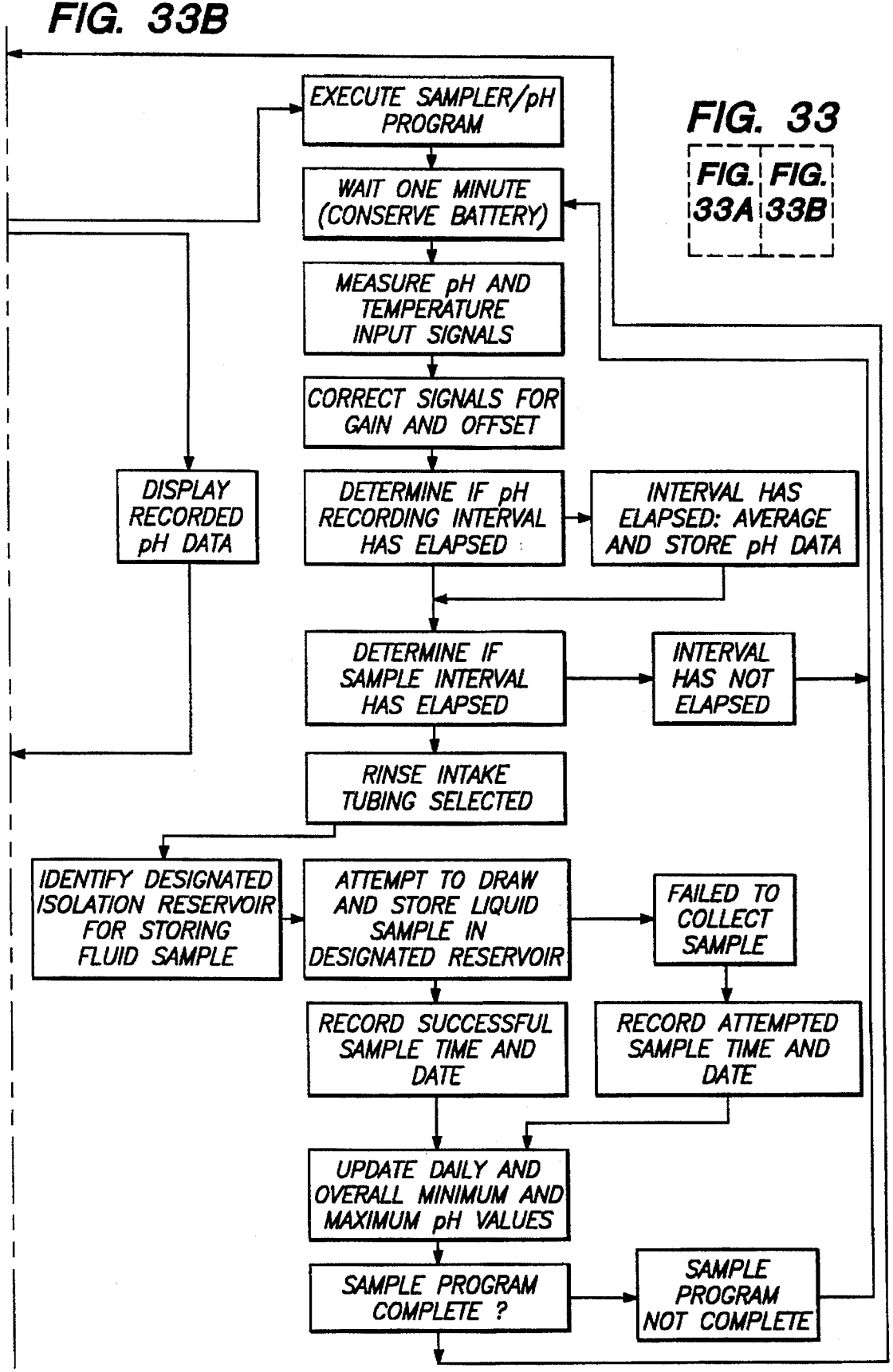

The fluid sample isolation means preferably but not necessarily includes programming means for allowing the user to designate the number of reservoirs 100 in which to store the isolated samples; to select the particular fluid variable to be monitored for the purposes of performing an isolated sampling operation, such as pH, dissolved oxygen content and conductivity; to select the control parameters or trigger point(s) pertaining to the selected fluid variable, the detection of which initiates the isolated sampling operation; and to select the ratio of collected fluid samples to designated isolated sampling reservoirs 100, together with fluid volume setting controls for the reservoirs 100. A representational flowchart detailing the a operational sequences is shown in FIG. 33 for the case of pH level being selected as the fluid variable which is monitored for isolation sampling.

Further, the present invention includes means for recording the time, date, and source of each isolated sample taken.

The fluid monitoring apparatus preferably but not necessarily includes means for maintaining collected samples of fluid at lowered temperatures, comprising an insulated housing; and means for cooling the housing to the desired temperature, including a thermostat, a compressor/condenser assembly and a forced air blower. Such an embodiment is substantially shown in FIG. 31. In a second embodiment, the fluid monitoring and collecting apparatus is portable having an insulated housing for the collected samples and a space defined therein for receiving ice or other substantially frozen articles so as to maintain the collected samples at substantially refrigerated temperatures.

The apparatus according to the invention may be selectively connected to an external pump so as to initiate a pumping operation when the fluid rises above a predetermined level as input by the user via keypad 3. It is further contemplated that the apparatus according to the invention may be selectively connected to an external rain guage. The computer control means of the apparatus may be provided with programming which permits the apparatus to initiate flow measurement based on rainfall as measured by signals received from the rain gauge, and or based on fluid depth and rainfall. Further, the apparatus is programmed to store rainfall data measured by the rain gauge in the RAM memory of the apparatus of the invention.

Figure 31:
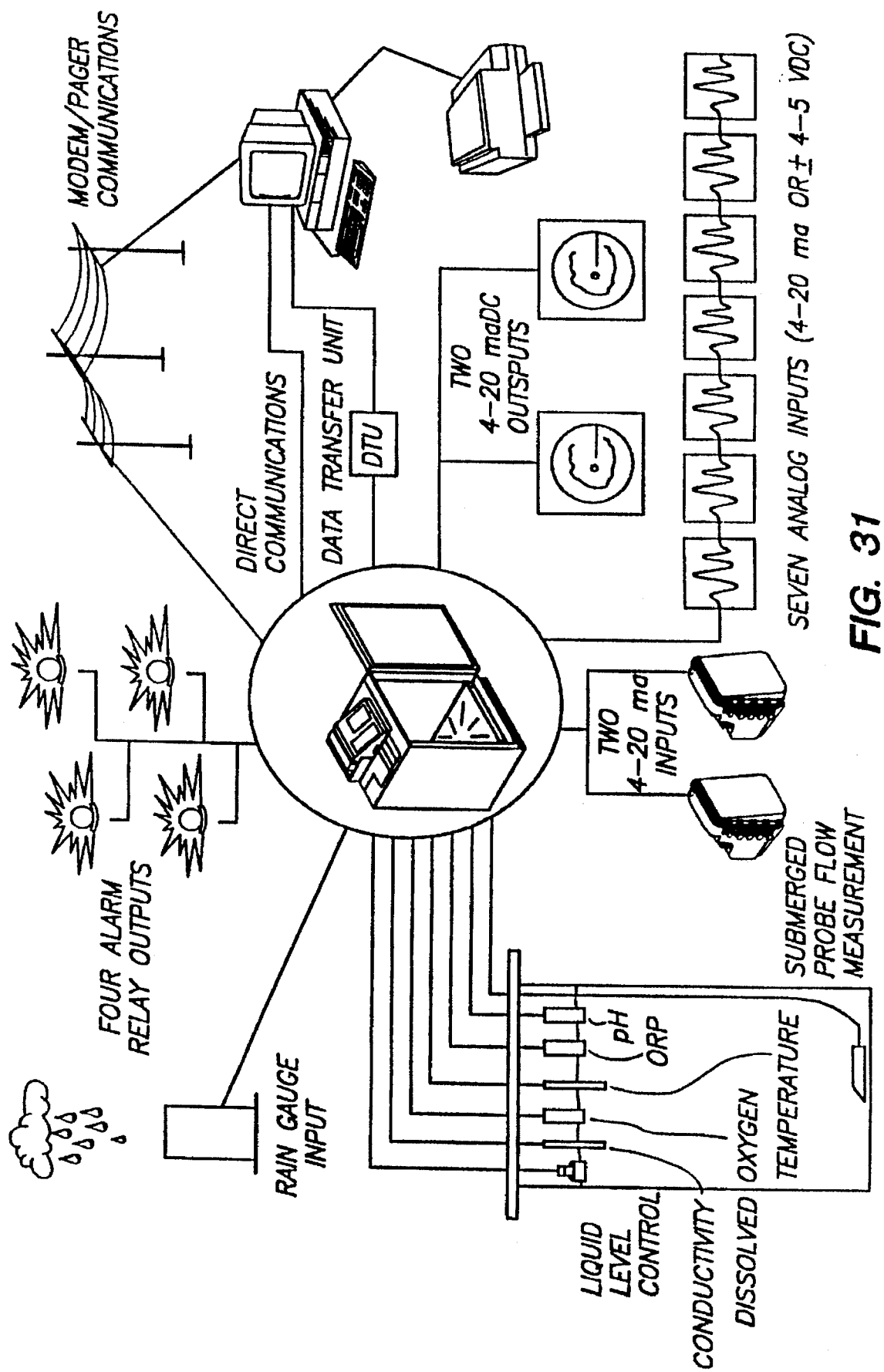
FIG. 31 is a perspective view of a preferred embodiment of the present invention.

With further reference to FIGS. 5 and 31, the fluid flow monitoring apparatus according to the invention is also desirably provided with at least one 4–20 mA output connection to enable the apparatus to form part of a current loop for driving a chart recorder or other external device. Preferably, an RS-232 standard type serial data interface and connection is also provided, to permit the apparatus to be connected with means for transferring recorded data as described below.

User Access to Stored Data

The user can request, via keypad 3, that data stored in RAM, such as flow related data, fluid condition data, and/or other data gathered from external devices linked to the apparatus, be displayed on display 4 when desired. Further, the combined text and graphics display 4 permits the user to selectively view data either in graphics or tabular form.

The invention provides an alternative means for retrieving stored data in the form of a portable data transfer unit, indicated as a "DTU" in FIG. 5. The portable data transfer unit is preferably very compact, i.e., pocket-sized, so that the user can conveniently carry same for selective use. The data transfer unit is provided with its own microprocessor, the memory of which may take the form of CMOS RAM chips powered by a lithium battery (battery backed-up RAM), or FLASH memory not requiting battery back-up. The data transfer unit is also preferably provided with its own user-input keypad and an alphanumeric display, and resembles a conventional small pocket calculator in overall appearance.

The data transfer unit is connected via a conventional connector cable (not shown) with the RS-232 serial connector. The user may then send an electronic data request command from the data transfer unit to the microprocessor of the apparatus. Upon receipt of such command, the microprocessor of the apparatus retrieves the requested data from its RAM and sends it for storage in the memory of the data transfer unit.

When it is desired to retrieve the data thus stored in the data transfer unit, the unit is in turn connected, via a standard computer or printer jack for example, to an external output device in the form of a conventional printer or computer (e.g., a personal computer). The stored data can be read out directly an a printer to produce a hard copy thereof, with the microprocessor of the data transfer unit itself operating the printer in a known manner. The user is thus able to obtain a complete and accurate hard copy record of the data. Alternatively, the stored data can be transferred to a conventional computer for manipulation using an available software program for statistical analyses, spreadsheet, etc.; for more permanent storage in a database stored in the computer's memory; and/or for printing by a printer connected to the computer.

As also shown in FIG. 5, an alternative data transfer means may be provided in the form of a modem which is built-in to the apparatus and provided with a standard external connector. The modem may comprise, for example, an FCC approved, 2400 baud modem with X modem feature. By virtue of the built-in modem, the apparatus can be linked by telephone line to a modem in a remote computer to permit immediate, long-distance transfer of stored data from a monitoring site.

Further, the fluid monitor apparatus preferably but not necessarily includes an alarm system for alerting the user of the occurrence of any of a number of events. As shown in FIG. 31, these alarms are preferably but not necessarily classified into two categories—alarms which are activated upon the occurrence of an out-of-range condition pertaining to one or more preselected fluid variables, and alarms pertaining to the effective operation of the apparatus. As to the latter category, an alarm may be activated upon the detection of a low battery, a modem failure, a missed sample, a purge failure, or a jammed distributor. The alarms may preferably set a relay or generate a report via the modem or RS-232 line, and may be selectively enabled.

Although it may not always be practical, the apparatus can alternatively be directly linked to a remote computer (e.g., a laptop computer) for direct transfer of the stored data from the apparatus to the computer.

It will be understood from the foregoing that the fluid monitoring apparatus according to the invention not only affords the unique capability of monitoring fluid flow on the basis of any desired one of a variety of different types of fluid flow sensor systems, but is also multi-functional in that it is capable of performing non-flow related operations such as fluid condition monitoring. The apparatus thus offers the user a wide variety of monitoring features in a single compact unit which is conveniently transported and easy to use.

While there have been described hereinabove what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

We claim:

1. A fluid velocity measurement device, comprising:
   means for transmitting an ultrasonic signal throughout a channel in which fluid flows;
   means for receiving a reflection of said ultrasonic signal, said reflected signal including signals which are shifted in frequency from said transmitted ultrasonic signal;
   means for generating an electrical signal from said reflected ultrasonic signal;
   first mixing means for mixing said reflected electrical signal with a signal having a frequency which is proportional to a frequency of said transmitted signal;
   first filtering means for filtering an output of said first mixing means so as to pass an audio band signal representative of said frequency shifted signal;
   means responsive to an output signal of said first filtering means, for substantially sequentially extracting energy levels therefrom at preselected frequencies within said audio band;
   means for computing an average fluid velocity value from said extracted energy levels;
   means for calculating a maximum velocity of fluid flow from said output signal of said first filtering means;
   means for verifying said computed average fluid velocity value based upon said maximum fluid velocity calculation; and
   means for reporting a value representing average fluid velocity in said channel based upon an output of said verifying means.

2. A device as recited in claim 1, wherein:
   said reporting means reports said computed average fluid velocity value if said computed average fluid velocity value is substantially proximal to said calculated maximum velocity value, and reports substantially said maximum velocity value if said average fluid velocity value is not substantially comparable to said maximum velocity value.

3. A device as recited in claim 1, wherein:
   said maximum velocity calculating means comprises a means for digitizing said output signal of said first filtering means, means for receiving an output signal of said digitizing means and for measuring a time duration of a plurality of substantially consecutive time periods thereof.

4. A device as recited in claim 3, wherein:
   said maximum velocity calculating means further includes means for selecting from said consecutive measured time periods those periods having the smallest duration, means for averaging said time periods having the smallest duration and for converting said average time duration to velocity, and means for reporting said converted velocity value as said maximum fluid velocity value.

5. A device as recited in claim 1, wherein:
   said average fluid velocity computing means includes a means for determining direction of fluid flow.

6. A device as recited in claim 1, wherein:
   said energy level extracting means comprises a means for generating an oscillating signal having a frequency proportional to a first input thereof; second mixing means for mixing said output signal from said first filtering means with an output from said oscillating means; second filtering means for filtering an output from said second mixing means so as to pass frequencies at an intermediate frequency; processing means for providing a plurality of values substantially sequentially to said first input of said oscillating means; and means for storing an output of said second filtering means.

7. A device as recited in claim 6, wherein:
   said oscillating means comprises a voltage controlled oscillator; and
   said processing means comprises a software controlled microprocessor.

8. A device as recited in claim 2, wherein:
   said reporting means reports said computed average fluid velocity value if said computed average fluid velocity value is greater than approximately 72% of said calculated maximum fluid velocity value, and reports substantially said calculated maximum velocity value if said computed average fluid velocity value is less than approximately 72% of said calculated maximum velocity value.

9. A device as recited in claim 8, wherein:
   said reporting means reports approximately 90% of said calculated maximum velocity value if said computed average fluid velocity value is less than approximately 72% of said calculated maximum velocity value.

10. A device as recited in claim 3, wherein:
    said time duration measuring means comprises a timer circuit and means for programmably controlling said timer circuit.

11. A device as recited in claim 1, wherein:
    said energy level extracting means comprises a microprocessor and a swept tuned local oscillator controlled by said microprocessor.

12. A device as recited in claim 5, wherein:
    said fluid flow direction means comprises a third mixing means for mixing said reflected electrical signal with a signal having a frequency which is proportional to a frequency of said transmitted signal and being shifted in phase therefrom, third filtering means for filtering an output of said third mixing means so as to pass a signal at a second intermediate frequency, and a means for detecting a phase difference between said first filtering means output and said third filtering means output.

13. An apparatus for monitoring at least one variable related to fluid in a channel, comprising:

an integral operating unit provided in a unitary case, said integral operating unit including computer means for controlling said apparatus and input means for receiving detected signals related to said fluid variable in said channel;

said input means being selectively connectable to any selected one or more of a plurality of different types of fluid-sensing means for producing signals related to said fluid variable in said channel;

said integral operating unit further including means for processing said signals from each of said plurality of different types of fluid sensing means, for input to said computer means;

said computer means comprising a microprocessor, program memory, and data memory, wherein:
said data memory stores user-selected input parameters including at least one fluid-related parameter; and
said microprocessor receives said signals related to said fluid from said processing means and calculates values of said fluid-related variable based on said signals and said user-input fluid-related parameter;

means for automatically sampling fluid from said channel and for storing said collected samples;

said user-selected input parameters include a predetermined value of said fluid-related variable;

said microprocessor generates control signals to initiate sampling operations by said automatic sampling means on the basis of said user-input predetermined value of said fluid-related variable or on the basis of a preselected time interval; and means for storing a fluid sample which is substantially isolated from other collected fluid samples.

14. An apparatus as recited in claim 13, further including:
means for maintaining collected fluid samples in said storing means at preselected temperatures.

15. An apparatus as recited in claim 14, wherein:
a portion of said unitary case is substantially insulated for storing collected fluid samples; and
said temperature maintaining means includes a means for refrigerating said insulated portion of said unitary case.

16. An apparatus as recited in claim 13, wherein:
said collected sample storing means comprises a plurality of reservoirs; and
said sample isolating means includes means for designating a number of said reservoirs for storing collected samples based upon a user-input predetermined value of said fluid-related variable, and for preventing collected samples pertaining to other fluid variables from being stored in said designated reservoirs.

17. An apparatus as recited in claim 13, wherein:
said computer means includes means for determining average fluid velocity within said channel, comprising:
a transducer for transmitting an ultrasonic signal and receiving a reflection thereof, said reflected signal having a frequency shifted component related to velocity of fluid flow;
first means for mixing said reflected signal;
means for filtering an output of said first means so as to extract said frequency shifted component therefrom;
means, responsive to said filtering means, for sequentially extracting energy levels of said frequency shifted component at preselected frequencies;
means for storing said energy levels; and
means for calculating average fluid velocity based upon said extracted energy levels of said frequency shifted component of said reflected signal.

18. An apparatus as recited in claim 17, wherein:
said average fluid velocity determining means includes means, responsive to an output of said filtering means, for calculating maximum fluid velocity in said channel, means for comparing said calculated average fluid velocity with said calculated maximum fluid velocity, and means for reporting a value representing average fluid velocity based upon said comparison.

19. An apparatus as recited in claim 18, wherein:
said maximum fluid velocity calculating means comprises a means for measuring and storing consecutive time periods of said frequency shifted component, means for selecting the smallest of said measured time periods, and means for averaging said smallest time periods.

20. An apparatus as recited in claim 17, wherein:
said sequential energy level extracting means comprises a swept tuned local oscillator, controlled by said microprocessor.

21. A device as recited in claim 1, further including:
means for sampling fluid flowing in said channel based upon said reported average fluid velocity value; and
means for storing fluid samples.

22. A device as recited in claim 21, wherein:
said fluid sampling means comprises a means for selecting one or more parameters related to fluid in said channel, means for comparing said fluid parameter to said reported average fluid velocity value, and means for initiating a fluid sample operation based upon said comparison.

23. A device as recited in claim 21, wherein:
said storing means selectively maintains collected fluid samples at any one of a plurality of temperatures.

24. A device as recited in claim 23, wherein:
a portion of said storing means is substantially insulated; and
said storing means includes a means for refrigerating said insulated portion of said storing means.

25. A device as recited in claim 22, wherein:
said storing means includes a means for storing a fluid sample which is substantially isolated from other collected fluid samples.

26. A device as recited in claim 25, wherein:
said fluid sample isolation means comprises a plurality of fluid containers, a means for designating a number of said fluid containers for storing collected samples based upon one of said selected fluid parameters of said fluid in said channel, and a means for substantially preventing collected samples pertaining to other said selected fluid parameters from being stored in said designated fluid containers.

27. A fluid velocity measurement device, comprising:
means for transmitting a signal throughout a channel in which fluid flows;
means for receiving a reflection of said signal, said reflected signal including signals which are shifted in frequency from said transmitted signal;
means for generating an electrical signal from said reflected signal;

first mixing means for mixing said electrical signal;

first filtering means for filtering an output of said first mixing means;

means responsive to an output signal of said first filtering means, for calculating energy levels thereof at selected frequencies;

means for computing an average fluid velocity value from said calculated energy levels; and means for calculating a maximum velocity of fluid flow from said output signal of said first filtering means.

* * * * *